US010485467B2

(12) United States Patent
Mitsuyoshi

(10) Patent No.: US 10,485,467 B2
(45) Date of Patent: Nov. 26, 2019

(54) ESTIMATION DEVICE, PROGRAM, ESTIMATION METHOD, AND ESTIMATION SYSTEM

(71) Applicants: PST CORPORATION, INC., Tokyo (JP); Shunji Mitsuyoshi, Tokyo (JP); JAPAN MATHEMATICAL INSTITUTE INC., Tokyo (JP)

(72) Inventor: Shunji Mitsuyoshi, Tokyo (JP)

(73) Assignees: PST CORPORATION, INC., Tokyo (JP); JAPAN MATHEMATICAL INSTITUTE INC., Tokyo (JP)

( * ) Notice: Subject to any disclaimer, the term of this patent is extended or adjusted under 35 U.S.C. 154(b) by 190 days.

(21) Appl. No.: 15/039,907

(22) PCT Filed: Nov. 28, 2014

(86) PCT No.: PCT/JP2014/005977
§ 371 (c)(1),
(2) Date: May 27, 2016

(87) PCT Pub. No.: WO2015/083357
PCT Pub. Date: Jun. 11, 2015

(65) Prior Publication Data
US 2017/0000397 A1    Jan. 5, 2017

(30) Foreign Application Priority Data

Dec. 5, 2013   (JP) .................................. 2013-251867

(51) Int. Cl.
*A61B 5/16*   (2006.01)
*A61B 5/0205*   (2006.01)
(Continued)

(52) U.S. Cl.
CPC ............ *A61B 5/165* (2013.01); *A61B 5/0205* (2013.01); *A61B 5/02055* (2013.01);
(Continued)

(58) Field of Classification Search
CPC combination set(s) only.
See application file for complete search history.

(56) References Cited

U.S. PATENT DOCUMENTS

2003/0028384 A1   2/2003 Kemp et al.
2007/0202477 A1   8/2007 Nakagawa
(Continued)

FOREIGN PATENT DOCUMENTS

CN   1455916 A   11/2003
CN   1838237 A   9/2006
(Continued)

OTHER PUBLICATIONS

DSM-IV and DSM-5 Criteria for the Personality Disorders, American Psychiatric Association, 2012.*
(Continued)

*Primary Examiner* — Scott Luan
(74) *Attorney, Agent, or Firm* — Oliff PLC

(57) ABSTRACT

Includes an extraction unit that extracts first information on a physiological state of a subject and second information on at least one of an emotion and organ activity of the subject from information on a physiology of the subject; a calculation unit that obtains a degree of similarity between changes over time indicated by the first information and the second information which are extracted and calculates a shift amount from a predetermined state in which a homeostasis in the subject is maintained based on the obtained degree of similarity; and an estimation unit that estimates a pathology of the subject based on the calculated shift amount.

16 Claims, 32 Drawing Sheets

(51) Int. Cl.
*A61B 7/04* (2006.01)
*A61B 5/00* (2006.01)
*G10L 17/26* (2013.01)
*A61B 5/01* (2006.01)
*A61B 5/021* (2006.01)
*A61B 5/024* (2006.01)
*A61B 5/0402* (2006.01)
*A61B 5/053* (2006.01)
*A61B 5/055* (2006.01)
*A61B 5/11* (2006.01)

(52) U.S. Cl.
CPC .......... *A61B 5/4255* (2013.01); *A61B 5/4803* (2013.01); *A61B 5/4857* (2013.01); *A61B 5/72* (2013.01); *A61B 5/7278* (2013.01); *A61B 5/741* (2013.01); *A61B 7/04* (2013.01); *G10L 17/26* (2013.01); *A61B 5/0077* (2013.01); *A61B 5/01* (2013.01); *A61B 5/021* (2013.01); *A61B 5/024* (2013.01); *A61B 5/02405* (2013.01); *A61B 5/0402* (2013.01); *A61B 5/055* (2013.01); *A61B 5/0531* (2013.01); *A61B 5/1103* (2013.01); *A61B 5/486* (2013.01); *A61B 5/7246* (2013.01); *A61B 5/7435* (2013.01); *A61B 2562/0204* (2013.01)

(56) References Cited

U.S. PATENT DOCUMENTS

| | | |
|---|---|---|
| 2007/0273504 A1 | 11/2007 | Tran |
| 2009/0210220 A1 | 8/2009 | Mitsuyoshi et al. |
| 2012/0083700 A1 | 4/2012 | Osorio |
| 2012/0116186 A1 | 5/2012 | Shrivastav et al. |
| 2013/0090927 A1 | 4/2013 | Quatieri et al. |

FOREIGN PATENT DOCUMENTS

| | | |
|---|---|---|
| JP | 2007-296169 A | 11/2007 |
| JP | 2012-000449 A | 1/2012 |
| JP | 2012-061057 A | 3/2012 |
| WO | 2006/132159 A1 | 12/2006 |
| WO | 2011/161672 A1 | 12/2011 |

OTHER PUBLICATIONS

Jun. 7, 2016 International Preliminary Report on Patentability issued in International Patent Application No. PCT/JP2014/005977.
Jul. 3, 2017 Office Action issued in Korean Patent Application No. 10-2016-7017552.
Jul. 10, 2017 Search Report issued in European Patent Application No. 14867047.4.
Nov. 13, 2017 Office Action issued in Russian Patent Applicaiton No. 2016126695.
Apr. 18, 2017 Office Action issued in Canadian Patent Application No. 2932689.
Feb. 17, 2015 Search Report issued in International Patent Application No. PCT/JP2014/005977.
Jan. 29, 2018 Office Action issued in Korean Patent Application No. 10-2016-7017552.
Sep. 14, 2018 Office Action issued in Chinese Patent Application No. 201480065678.6.
Jul. 27, 2018 Office Action issued in Russian Patent Application No. 2016126695.
Mar. 21, 2018 Office Action issued in Chinese Patent Application No. 201480065678.6.
Mar. 30, 2018 Office Action issued in Russian Patent Application No. 2016126695.

* cited by examiner

FIG. 19
REGION A
In case where balanced position P1 is in region between Pleasure – Sorrow (counterclockwise)
(a)
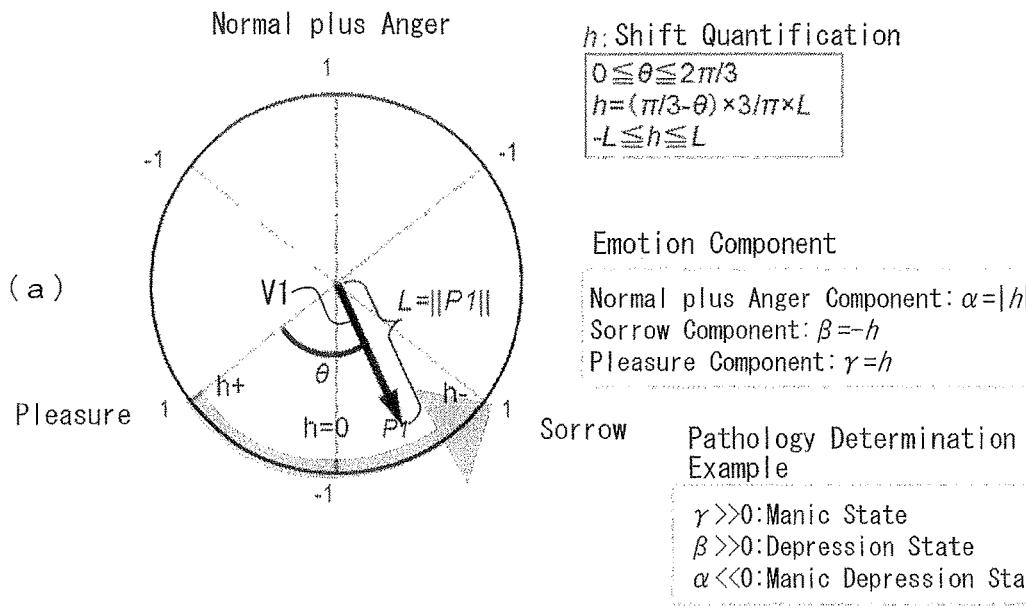
REGION B
In case where balanced position P1 is in region between Pleasure – Sorrow (clockwise)
(b)
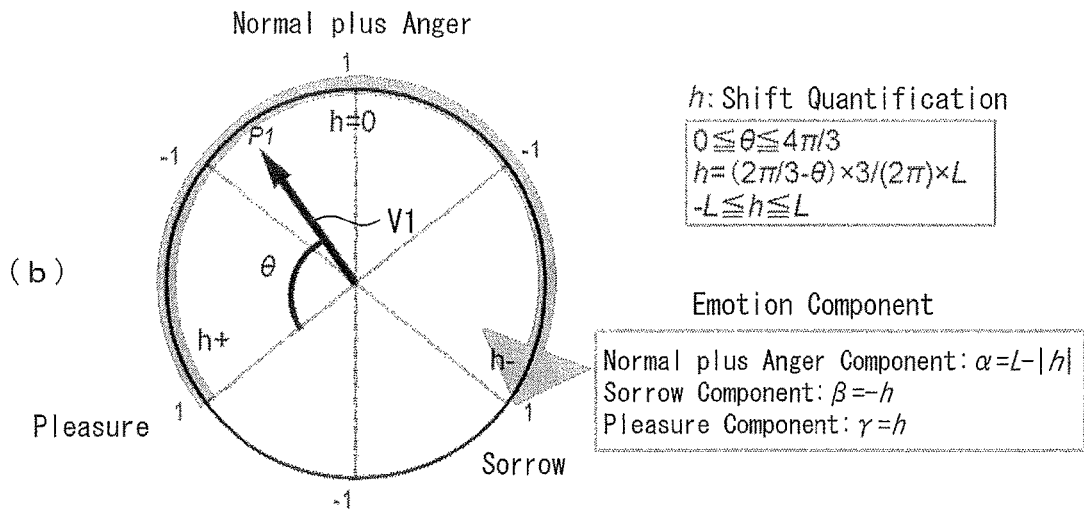

FIG. 23

| Date | Circ. Sys. K1 | Circ. Sys. K2 | Circ. Sys. K3 | Circ. Sys. K4 | Circ. Sys. K5 | Circ. Sys. K6 | Circ. Sys. K7 | Circ. Sys. K8 | Circ. Sys. K9 | Circ. Sys. K10 |
|---|---|---|---|---|---|---|---|---|---|---|
| .. | .. | .. | .. | .. | .. | .. | .. | .. | .. | .. |
| 2013/10/29 09:10:00 | +0.4 | -0.2 | +1.5 | -1.0 | -3.2 | +1.2 | +2.9 | -0.7 | +2.1 | -1.2 |
| 2013/10/29 10:10:00 | -0.7 | -0.5 | +1.0 | -1.7 | -2.8 | +1.6 | +3.6 | -1.0 | +1.4 | -1.4 |
| 2013/10/29 11:10:00 | -1.2 | +0.1 | +0.7 | -1.3 | -2.0 | +0.9 | +3.0 | -1.2 | +1.2 | -2.1 |
| 2013/10/29 12:10:00 | -1.8 | +0.4 | +0.3 | -0.5 | -2.2 | +0.3 | +3.5 | -0.9 | +0.6 | -1.5 |
| 2013/10/29 13:10:00 | -1.3 | +0.5 | +1.1 | -2.0 | -1.9 | -0.4 | +3.1 | -0.9 | -0.2 | -0.9 |
| .. | .. | .. | .. | .. | .. | .. | .. | .. | .. | .. |

| Date | Circ. Sys. Ka1 [rpm] | Circ. Sys. Ka2 [rpm] | Circ. Sys. Ka3 [rpm] | Circ. Sys. Ka4 [rmp] |
|---|---|---|---|---|
| ⋮ | ⋮ | ⋮ | ⋮ | ⋮ |
| 2013/10/29 09:10:00 | 20 | 15 | 10 | 4 |
| 2013/10/29 09:11:00 | 50 | 20 | 8 | 3 |
| 2013/10/29 09:12:00 | 10 | 7 | 10 | 5 |
| 2013/10/29 09:13:00 | 0 | 0 | 0 | 0 |
| 2013/10/29 09:14:00 | 10 | 30 | 5 | 3 |
| ⋮ | ⋮ | ⋮ | ⋮ | ⋮ |

FIG. 28

| Pathology | Circ. Sys. Ka1 [rpm] | Circ. Sys. Ka2 [rpm] | Circ. Sys. Ka3 [rpm] | Circ. Sys. Ka4 [rpm] |
|---|---|---|---|---|
| Major Depression | R1=0 | R2=0 | R3=0 | R4=0 |
| Depression | — | — | $R3 < \alpha$ | — |
| Normal | — | — | $\alpha \leq R3 \leq \beta$ | — |
| Manic Depression | — | — | $R3 > \beta$ | — |
| Personality Disorder | R1=R4 | — | — | R4=R1 |
| ⋮ | ⋮ | ⋮ | ⋮ | ⋮ |

| Pathology | Utterance |
|---|---|
| Major Depression | GO TO HOSPITAL QUICKLY. |
| Depression | DON'T JUST STAY AT HOME. LET'S GO FOR A WALK OUTSIDE ONCE IN A WHILE. |
| Personality Disorder (Male) | YOU MUST THINK ABOUT NOT ONLY YOURSELF BUT ALSO OTHER PERSON'S FEELING. |
| Personality Disorder (Female) | YOU ARE ALWAYS DOING YOUR BEST. SO, STOP DOING SUCH A THING. |
| ⋮ | ⋮ |

80

ESTIMATION DEVICE, PROGRAM, ESTIMATION METHOD, AND ESTIMATION SYSTEM

CROSS REFERENCE TO RELATED APPLICATION

This application is a U.S. National Stage application claiming the benefit of prior filed International Application Number PCT/JP2014/005977, filed on Nov. 28, 2014, in which the International Application claims priority from Japanese Patent Application Number 2013-251867, filed on Dec. 5, 2013, the entire contents of which are incorporated herein by reference.

TECHNICAL FIELD

The present invention relates to an estimation device that estimates the pathology of a subject, a program, an estimation method, and an estimation system.

BACKGROUND ART

In recent years, a technique has been proposed in which a sound signal of a subject or an electrical signal indicating the activity of an organ such as the heart is measured, an emotion and organ activity of the subject are obtained from the measured signal, and the pathology of the subject is estimated based on changes over time in the obtained emotion and organ activity (for example, see Patent Documents 1 and 2).
Patent Document 1: International Publication No. 2006/132159
Patent Document 2: Japanese Unexamined Patent Application No. 2012-61057

DISCLOSURE

Problems to be Solved

However, in the related art, a user is required to have expert knowledge on medicine in estimating the pathology of a subject based on changes over time in an emotion and organ activity of the subject which are obtained from the measured signal.

In one aspect, propositions of the estimation device, program, estimation method, and estimation system of the present disclosure are to easily estimate the pathology of a subject without having expert knowledge.

Means for Solving the Problems

An estimation device according to an aspect includes an extraction unit that extracts first information on a physiological state of a subject and second information on at least one of an emotion and organ activity of the subject from information on a physiology of the subject; a calculation unit that obtains a degree of similarity between changes over time indicated by the first information and the second information which are extracted, and calculates a shift amount from a predetermined state in which a homeostasis in the subject is maintained based on the obtained degree of similarity; and an estimation unit that estimates a pathology of the subject based on the calculated shift amount.

A program according to another aspect causes a computer to execute a process of extracting first information on a physiological state of a subject and second information on at least one of an emotion and organ activity of the subject from information on a physiology of the subject; obtaining a degree of similarity between changes over time indicated by the first information and the second information which are extracted, and calculating a shift amount from a predetermined state in which a homeostasis in the subject is maintained based on the obtained degree of similarity; and estimating a pathology of the subject based on the calculated shift amount.

An estimation method according to another aspect causes an extraction unit to extract first information on a physiological state of a subject and second information on at least one of an emotion and organ activity of the subject from information on a physiology of the subject; a calculation unit to obtain a degree of similarity between changes over time indicated by the first information and the second information which are extracted, and to calculate a shift amount from a predetermined state in which a homeostasis in the subject is maintained, based on the obtained degree of similarity; and estimation unit to estimate a pathology of the subject based on the calculated shift amount.

An estimation system according to another aspect includes a measurement device that measures a physiology of a subject, an estimation device that estimates a pathology of the subject using information on the physiology of the subject which is measured by the measurement device, and an output device that outputs a result of the pathology estimated by the estimation device, and in which the estimation device includes an extraction unit that extracts first information on a physiological state of a subject and second information on at least one of an emotion and organ activity of the subject from information on a physiology of the subject, a calculation unit that obtains a degree of similarity between changes over time indicated by the first information and the second information which are extracted, and calculates a shift amount from a predetermined state in which a homeostasis in the subject is maintained based on the obtained degree of similarity, and an estimation unit that estimates a pathology of the subject based on the calculated shift amount.

The estimation device, program, estimation method, and estimation system of the present disclosure can allow the pathology of a subject to be easily estimated without having expert knowledge.

BRIEF DESCRIPTION OF DRAWINGS

FIG. 19 is a diagram illustrating another example of homeostasis of a subject's emotion.

FIG. 23 is a diagram illustrating an example of data of displacement of each circulation system of a subject.

FIG. 27 is a diagram illustrating an example of data of the number of rotations of each circulation system of a subject.

FIG. 28 is a diagram illustrating an example of a pathology table.

FIG. 31 is a diagram illustrating an example of an utterance table.

DETAILED DESCRIPTION OF THE EMBODIMENTS

Hereinafter, embodiments will be described with reference to the accompanying drawings.

Figure 1:
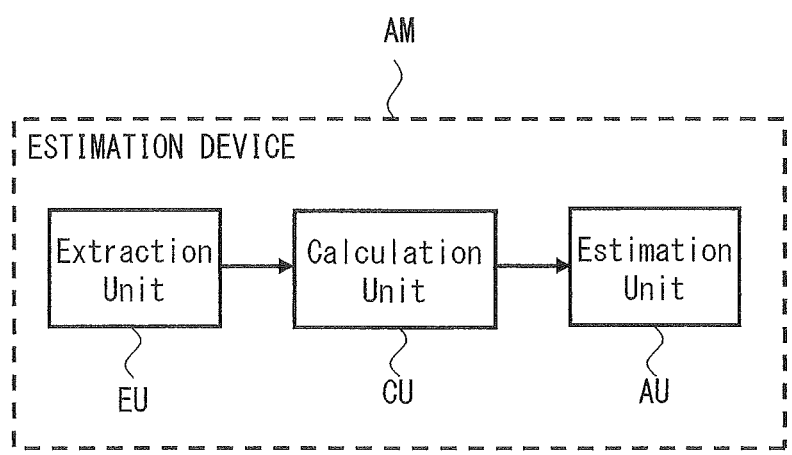
FIG. 1 is a diagram illustrating an estimation device according to an embodiment.

FIG. 1 illustrates an estimation device according to an embodiment.

An estimation device AM illustrated in FIG. 1 is a computer device or the like which includes an arithmetic processor such as a Central Processing Unit (CPU) and a storage device such as a hard disk device. The estimation device AM includes an extraction unit EU, a calculation unit CU, and an estimation unit AU. Functions of the extraction unit EU, the calculation unit CU, and the estimation unit AU may be realized by a program executed by a CPU or may be realized by hardware.

The extraction unit EU extracts first information indicating a pitch frequency of a sound, a fundamental frequency, or a subject's physiological state such as body temperature or heart rate, from information indicating the physiology of a subject including sound data uttered by the subject or data such as body temperature or a heartbeat which is stored in a storage device of the estimation device AM. In addition, the extraction unit EU extracts second information indicating at least one of a subject's emotion including anger or sorrow and the activity of an organ such as a subject's heart or bowel, from information indicating the physiology of the subject.

The calculation unit CU obtains the degree of similarity between changes over time indicated by the first information and the second information which are extracted, to thereby calculate a shift amount (hereinafter, referred to as a shift amount of homeostasis) from a predetermined state in which a homeostasis in a subject is maintained, based on the obtained degree of similarity.

The estimation unit AU estimates the pathology of a subject based on the calculated shift amount of homeostasis. In addition, the estimation device AM outputs information indicating the pathology estimated by the estimation unit AU to an external display such as an Organic Electro-Luminescence (EL) or a liquid crystal.

As described above, in the embodiment illustrated in FIG. 1, a shift amount of homeostasis in a subject is calculated using first information indicating a subject's physiological state and second information indicating at least one of a subject's emotion and organ activity. Thereby, the estimation device AM can easily estimate the pathology of a subject without having expert knowledge on medicine with reference to one index such as a shift amount of homeostasis.

Figure 2:
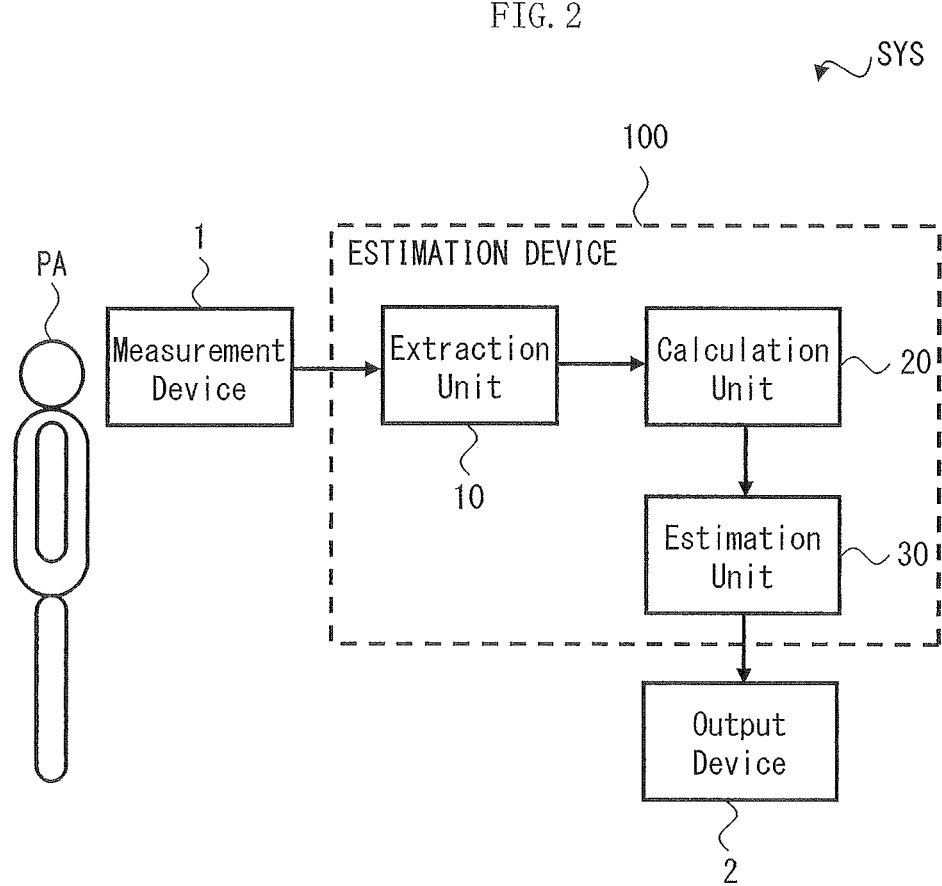
FIG. 2 is a diagram illustrating an estimation device according to another embodiment.

FIG. 2 illustrates an estimation device according to another embodiment.

An estimation device 100 illustrated in FIG. 2 is a computer device or the like which includes an arithmetic processor such as a CPU and a storage device such as a hard disk device. The estimation device 100 is connected to a measurement device 1 and an output device 2 in a wired or wireless manner through an interface unit included in the estimation device 100. Thereby, for example, the estimation device 100, the measurement device 1, and the output device 2 operate as an estimation system SYS.

The measurement device 1 includes, for example, at least a microphone, and measures information indicating the physiology of a subject PA. For example, the measurement device 1 measures a sound signal uttered by the subject PA through the microphone, and outputs the measured sound signal to the estimation device 100 as information indicating the physiology of the subject PA.

The output device 2 includes a display such as an organic EL or a liquid crystal. The output device 2 receives an estimation result of the pathology of the subject PA which is obtained by the estimation device 100, and displays the received estimation result on the display such as an organic EL. Meanwhile, the output device 2 may be provided inside the estimation device 100.

The estimation device 100 illustrated in FIG. 2 includes an extraction unit 10, a calculation unit 20, and an estimation unit 30. Functions of the extraction unit 10, the calculation unit 20, and the estimation unit 30 may be realized by a program executed by a CPU or may be realized by hardware.

The extraction unit 10 extracts first information indicating a physiological state of the subject PA and second information indicating at least one of an emotion of the subject PA and the activity of an organ such as the heart or bowel of the subject PA, from information indicating the physiology of the subject PA which is measured by the measurement device 1. The extraction unit 10 outputs the first information and the second information which are extracted to the calculation unit 20. The operation of the extraction unit 10 will be described with reference to FIGS. 3 to 7.

The calculation unit 20 calculates the degree of similarity between changes over time in the first information and the second information which are extracted. For example, the calculation unit 20 performs a mutual correlation process of changes over time in the first information and the second information which are extracted, to thereby calculate mutual correlation coefficients as degrees of similarity. The calculation unit 20 obtains a shift amount of homeostasis in the subject PA using the calculated plurality of degrees of similarity. The operation of the calculation unit 20 and a homeostasis will be described with reference to FIGS. 8 to 12.

The estimation unit 30 estimates the pathology of the subject PA based on the obtained shift amount of homeostasis in the subject PA. The estimation unit 30 outputs information indicating the estimated pathology of the subject PA to the output device 2. The operation of the estimation unit 30 will be described with reference to FIGS. 12 to 16.

Figure 3:
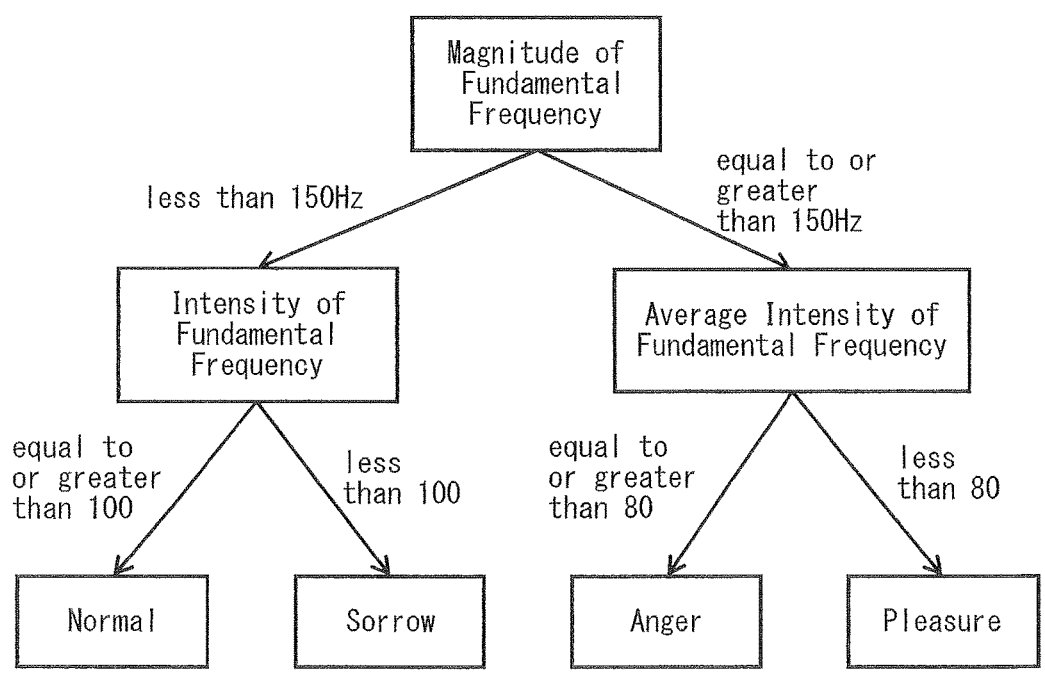
FIG. 3 is a diagram illustrating an example of a determination tree showing a relationship between a fundamental frequency of a subject's utterance and the subject's emotion.

FIG. 3 illustrates an example of a determination tree illustrating a relationship between a fundamental frequency of utterance of the subject PA and an emotion of the subject PA. The determination tree illustrated in FIG. 3 is generated based on, for example, an emotion of each of a plurality of (for example, 100 or more) subjects PA which is subjectively evaluated to be any of "normal", "sorrow", "anger", "pleasure", and the like for each utterance of the subject PA, the magnitude of the extracted fundamental frequency, and the like. That is, the determination tree illustrated in FIG. 3 indicates a relationship between emotions of normal, sorrow, anger, and pleasure and the magnitude, intensity, and average intensity of a fundamental frequency in utterance. For example, in the emotion of normal, the magnitude of a fundamental frequency is less than 150 hertz, and the intensity of the fundamental frequency is equal to or greater than 100. In the emotion of sorrow, the magnitude of a fundamental frequency is less than 150 hertz, and the intensity of the fundamental frequency is less than 100. In the emotion of anger, the magnitude of a fundamental frequency is equal to or greater than 150 hertz, and the average intensity of the fundamental frequency is equal to or greater than 80. In the emotion of pleasure, the magnitude of a fundamental frequency is equal to or greater than 150 hertz, and the intensity of the fundamental frequency is less than 80.

Meanwhile, the determination tree illustrated in FIG. 3 is stored in the storage device of the estimation device 100 in advance. In addition, in the determination tree illustrated in FIG. 3, emotions of the subject PA include normal, sorrow, anger, and pleasure, but may also include emotions such as uneasiness and pain. In addition, the estimation device 100 may have a determination tree indicating a relationship between a sound parameter such as a pitch frequency and an emotion.

For example, the extraction unit 10 performs frequency analysis such as Fast Fourier Transform (FFT) on a sound signal of utterance of the subject PA which is received from the measurement device 1 to obtain the magnitude of a fundamental frequency, and the like. The extraction unit 10 obtains a ratio of each of emotions of normal, sorrow, anger, and pleasure that appear in the subject PA at the moment of each utterance in a range of values of, for example, 0 to 10, based on the magnitude of the fundamental frequency, and the like, which are obtained from each utterance of the subject PA, and the determination tree illustrated in FIG. 3. Meanwhile, the sum of the ratios of the emotions of normal, sorrow, anger, and pleasure has a fixed value, and is set to, for example, 10. In addition, the ratios of normal, sorrow, anger, pleasure may have values falling outside the range of values of 0 to 10.

In addition, the extraction unit 10 obtains an intonation, a pitch frequency, and the like from a sound signal of the subject. PA. For example, the extraction unit 10 detects regions having the same frequency component from a pattern of a change in intensity in an utterance unit of a sound signal, and acquires a time interval at which the detected regions having the same frequency component appear, as an intonation. In addition, for example, the extraction unit 10 acquires a frequency spectrum from the frequency analysis of a sound signal. The extraction unit 10 performs an autocorrelation process while shifting the acquired frequency spectrum on a frequency axis to obtain the waveform of an autocorrelation coefficient. The extraction unit 10 obtains a pitch frequency based on an interval between crests or between troughs in the obtained waveform of the autocorrelation coefficient. In addition, the extraction unit 10 obtains the degree of excitement (hereinafter, referred to as an excitement degree) of the subject PA in a range of values of 0 to 10, from comparison between the obtained intonation and pitch frequency and a predetermined interval and frequency. The excitement degree increases as an interval of appearance in the same frequency component indicated by the intonation becomes shorter than the predetermined interval or as the pitch frequency becomes higher than the predetermined frequency. In other words, physiological excitement of the subject PA and the activity of cranial nerves such as sympathetic nerves and parasympathetic nerves of the subject PA are closely related with each other, and thus it is possible to examine a relationship between the activity of cranial nerves of the subject PA and an emotion of the subject PA. Meanwhile, the excitement degree may have a value falling outside the range of values of 0 to 10.

For example, the extraction unit 10 multiplies the obtained excitement degree by a ratio of each of normal, sorrow, anger, and pleasure to obtain the intensity of each of normal, sorrow, anger, and pleasure. The excitement degree is an example of first information, and the intensity of each of normal, sorrow, anger, and pleasure is an example of second information.

FIGS. 4 to 7 illustrate an example of a change over time in the intensity of each of an excitement degree, normal, sorrow, anger, and pleasure for each subject PA. The horizontal axis in each of FIGS. 4 to 7 represents the order of utterance units of the subject PA as a time axis, and the vertical axis in each of FIGS. 4 to 7 represents the intensity of each of an excitement degree, and normal, sorrow, anger, and pleasure. A solid line represents a change over time in an excitement degree, and a dashed line represents a change over time in a value (hereinafter, also referred to as "normal plus anger") which is obtained by adding the intensity of normal to the intensity of anger. In addition, a dotted line represents a change over time in the intensity of sorrow, and a broken line represents a change over time in the intensity of pleasure.

Meanwhile, a change over time in the intensity of each of an excitement degree, normal plus anger, sorrow, and pleasure illustrated in FIGS. 4 to 7 represents, for example, a value obtained by moving average with a window width of 10 utterance units by the calculation unit 20.

In addition, the adding of the intensities of normal and anger is for the purpose of allowing the inventor to estimate that a characteristic change appears in emotions of sorrow and pleasure in estimating whether or not the subject PA suffers from a psychiatric disorder and to treat normal and anger as other emotions. Meanwhile, the emotions of normal and anger may also be examined individually, similar to sorrow and pleasure.

Figure 4:
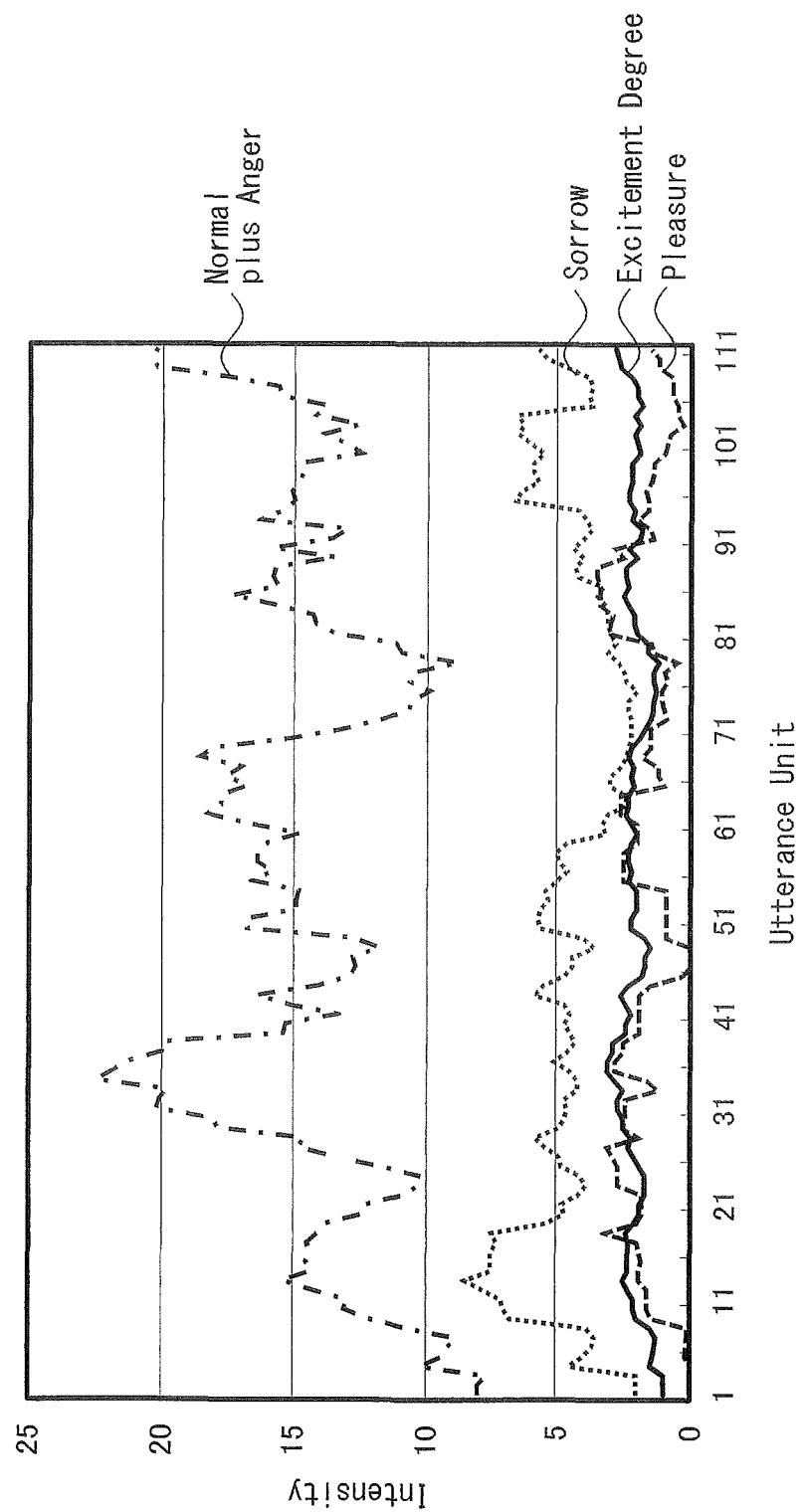
FIG. 4 is a diagram illustrating an example of a change over time in the intensity of each of an excitement degree, normal, sorrow, anger, and pleasure of a doctor.

FIG. 4 illustrates a change over time in the intensity of each of an excitement degree, normal, sorrow, anger, and pleasure when a subject PA is a healthy psychiatrist who does not suffer from a psychiatric disorder and examines a melancholiac. As illustrated in FIG. 4, the excitement degree of the doctor who is a subject PA indicates a fluctuation in a range of 1 to 3.5 during utterance. In addition, in the doctor's emotion, the intensity of normal plus anger has a value larger than those of sorrow and pleasure during utterance, and the intensity of pleasure has a value smaller than that of sorrow as a whole because the doctor examines the melancholiac.

Figure 5:
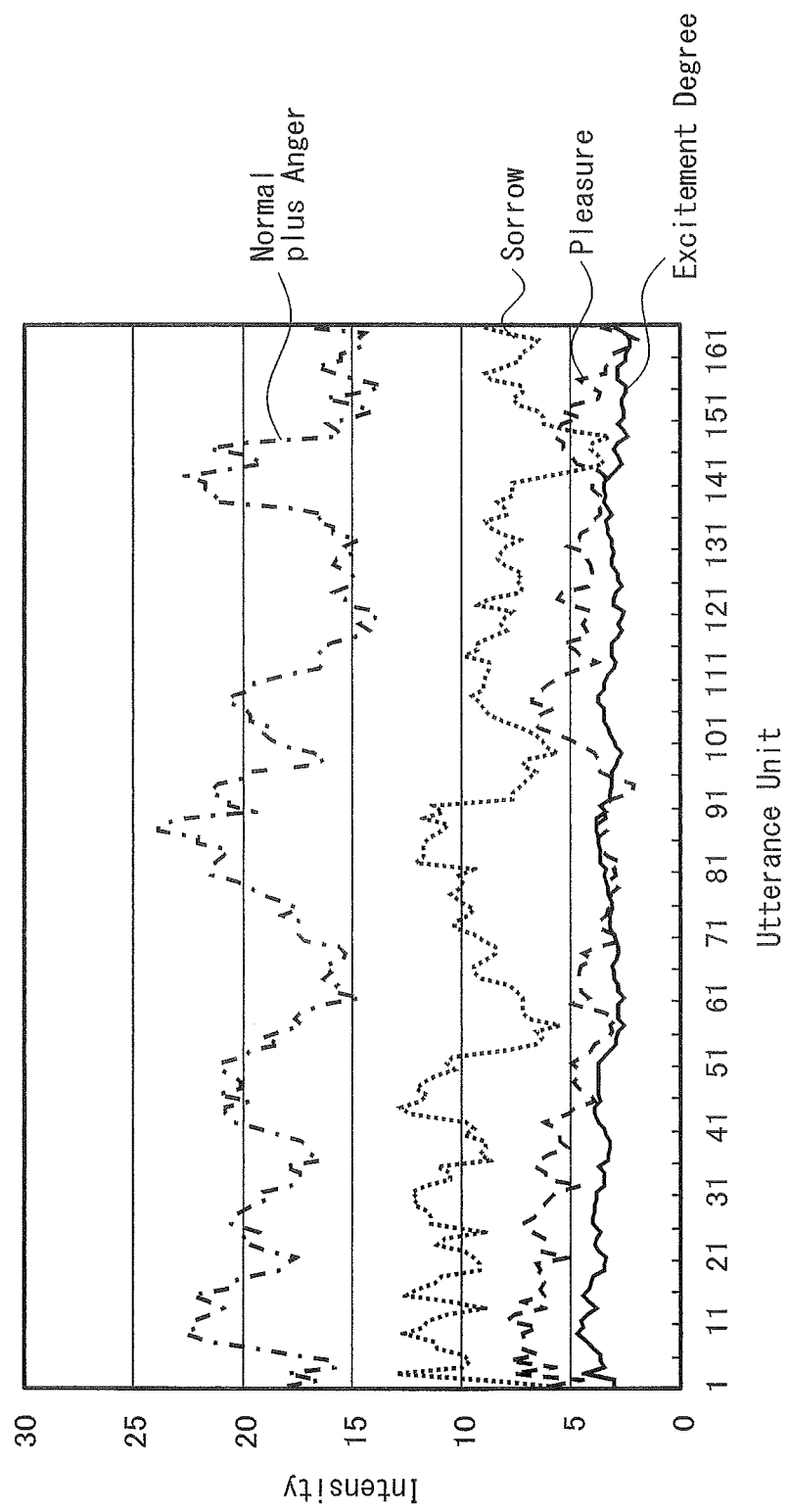
FIG. 5 is a diagram illustrating an example of a change over time in the intensity of each of an excitement degree, normal, sorrow, anger, and pleasure of a melancholiac.

FIG. 5 illustrates a change over time in the intensity of each of an excitement degree, normal, sorrow, anger, and pleasure when a subject PA is a melancholiac and is examined by the doctor illustrated in FIG. 4. As illustrated in FIG. 5, the excitement degree of the melancholiac who is a subject PA indicates a fluctuation in a range of 2 to 5 during utterance, and has a value larger than that of an excitement degree of the doctor illustrated in FIG. 4. In addition, in the melancholiac's emotion, the intensity of normal plus anger has a value larger than those of sorrow and pleasure during utterance, and the intensity of sorrow has a value larger than that of the intensity of pleasure. In addition, the intensities of sorrow and pleasure of the melancholiac have values larger than those in the case of the doctor illustrated in FIG. 4.

Figure 6:
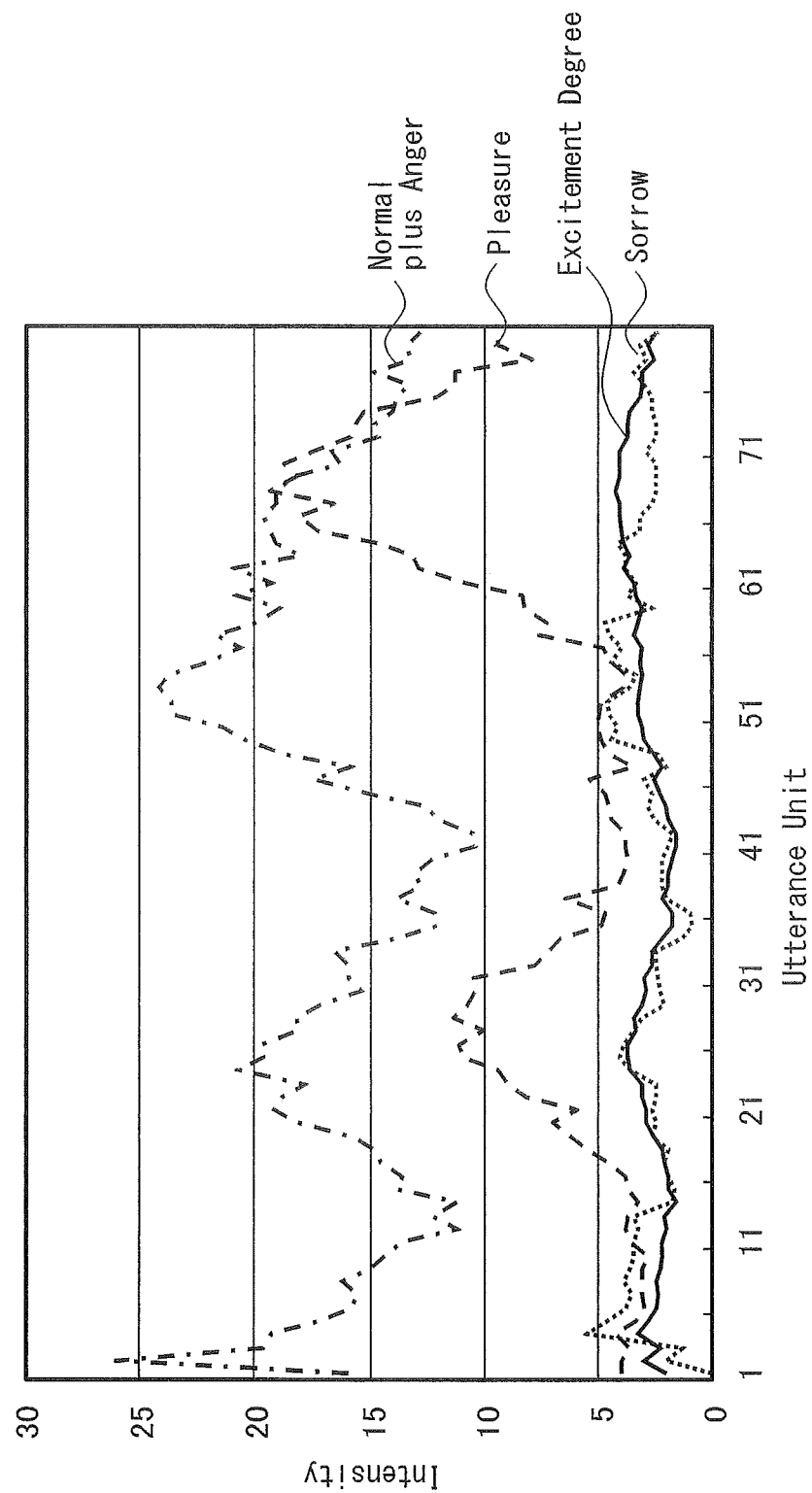
FIG. 6 is a diagram illustrating an example of a change over time in the intensity of each of an excitement degree, normal, sorrow, anger, and pleasure of an ordinary person.

FIG. 6 illustrates a change over time in the intensity of each of an excitement degree, normal, sorrow, anger, and pleasure when a subject PA is a healthy ordinary person A who does not suffer from a psychiatric disorder. As illustrated in FIG. 6, the excitement degree of the ordinary person A who is a subject PA indicates a fluctuation in a range of 1.5 to 4.5. In addition, the emotion of the ordinary person A indicates that the intensity of normal plus anger is larger than those of sorrow and pleasure during utterance, similar to the case of the doctor illustrated in FIG. 4 and the case of the melancholiac illustrated in FIG. 5. On the other hand, the intensity of pleasure in the ordinary person A has a value larger than that of the intensity of sorrow. Further, as illustrated in FIG. 6, the intensity of pleasure of the ordinary person A is distributed in a range of values larger than those in the case of the doctor illustrated in FIG. 4 and the case of the melancholiac illustrated in FIG. 5, and the intensity of sorrow of the ordinary person A is distributed in a range of values smaller than those in the case of the doctor illustrated in FIG. 4 and the case of the melancholiac illustrated in FIG. 5.

Figure 7:
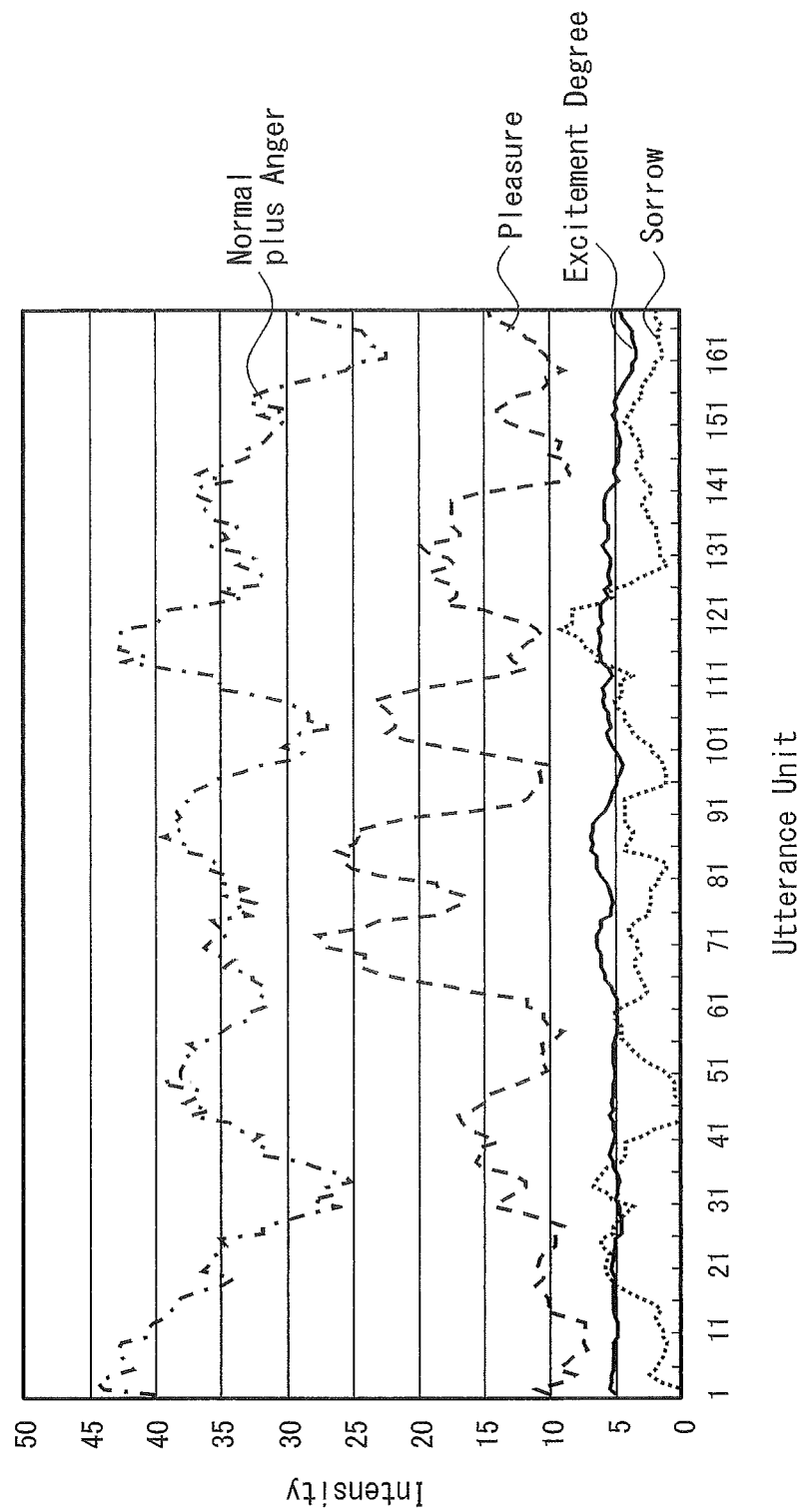
FIG. 7 is a diagram illustrating an example of a change over time in the intensity of each of an excitement degree, normal, sorrow, anger, and pleasure of an ordinary person which are different from those of the ordinary person illustrated in FIG. 6.

FIG. 7 illustrates a change over time in the intensity of each of an excitement degree, normal, sorrow, anger, and pleasure when a subject PA is a healthy ordinary person B who is different from the ordinary person A illustrated in FIG. 6 and does not suffer from a psychiatric disorder. As illustrated in FIG. 7, the excitement degree of the ordinary person B who is a subject PA indicates a fluctuation in a range of 3 to 7. In addition, in the emotion of the ordinary person B, the intensity of normal plus anger has a value larger than those of sorrow and pleasure during utterance, similar to the case of the ordinary person A illustrated in FIG. 6. In addition, the intensity of pleasure of the ordinary person B has a value larger than the intensity of sorrow, similar to the case of the ordinary person A illustrated in FIG. 6.

For example, the calculation unit 20 performs a mutual correlation process between a change over time in an excitement degree and a change over time in the intensity of each of normal plus anger, sorrow, and pleasure in each subject PA illustrated in FIGS. 4 to 7. The calculation unit 20 obtains a mutual correlation coefficient between an excitement degree of each subject PA and the intensity of each of normal plus anger, sorrow, and pleasure. Meanwhile, a window width of a mutual correlation process performed by the calculation unit 20 is set to, for example, 150 utterances, but may be set for each subject PA or in accordance with a required processing speed, the accuracy of estimation, or the like.

FIGS. 8 to 11 illustrate an example of results of a mutual correlation process between an excitement degree and each emotion in a subject PA which is performed by the arithmetic operation unit 20 illustrated in FIG. 2. The horizontal axis in each of FIGS. 8 to 11 represents the order of utterance units of the subject PA as a time axis, and the vertical axis in each of FIGS. 8 to 11 represents a mutual correlation coefficient. In addition, a dashed line represents a change over time in a mutual correlation coefficient between an excitement degree and the intensity of normal plus anger, a dotted line represents a change over time in a mutual correlation coefficient between an excitement degree and the intensity of sorrow, and a broken line represents a change over time in a mutual correlation coefficient between an excitement degree and the intensity of pleasure.

Figure 8:
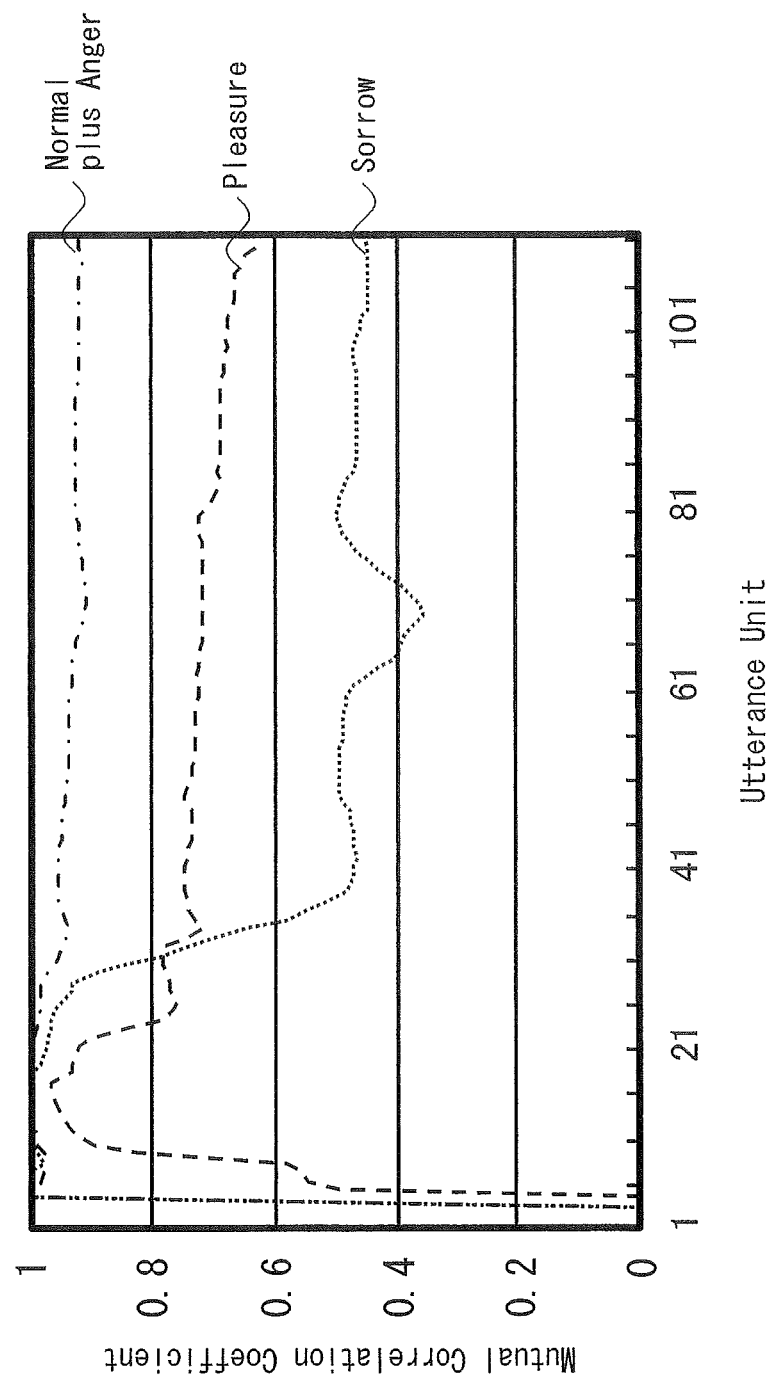
FIG. 8 is a diagram illustrating an example of results of a mutual correlation process between the degree of excitement and each emotion of the doctor illustrated in FIG. 4 which is performed by a calculation unit illustrated in FIG. 2.

FIG. 8 illustrates a change over time in a mutual correlation coefficient between an excitement degree of the doctor illustrated in FIG. 4 and the intensity of each of normal plus anger, sorrow, and pleasure. In the doctor illustrated in FIG. 8, a mutual correlation coefficient of normal plus anger has a value larger than those in the case of pleasure and sorrow, and a mutual correlation coefficient of sorrow has the smallest value in a 40 utterance unit and the subsequent utterance units. Meanwhile, since the number of pieces of data of the excitement degree and each emotion of the doctor in a window width (for example, 150 utterance unit) of the mutual correlation process is small between the start of utterance and the 40 utterance unit, a value of a mutual correlation coefficient between the excitement degree calculated by the calculation unit 20 and each emotion is not stabilized, and thus the reliability of a calculation result is low. For this reason, in the following description, mutual correlation coefficients in the 40 utterance unit and the subsequent utterance units are used in the case of the doctor illustrated in FIG. 8.

Figure 9:
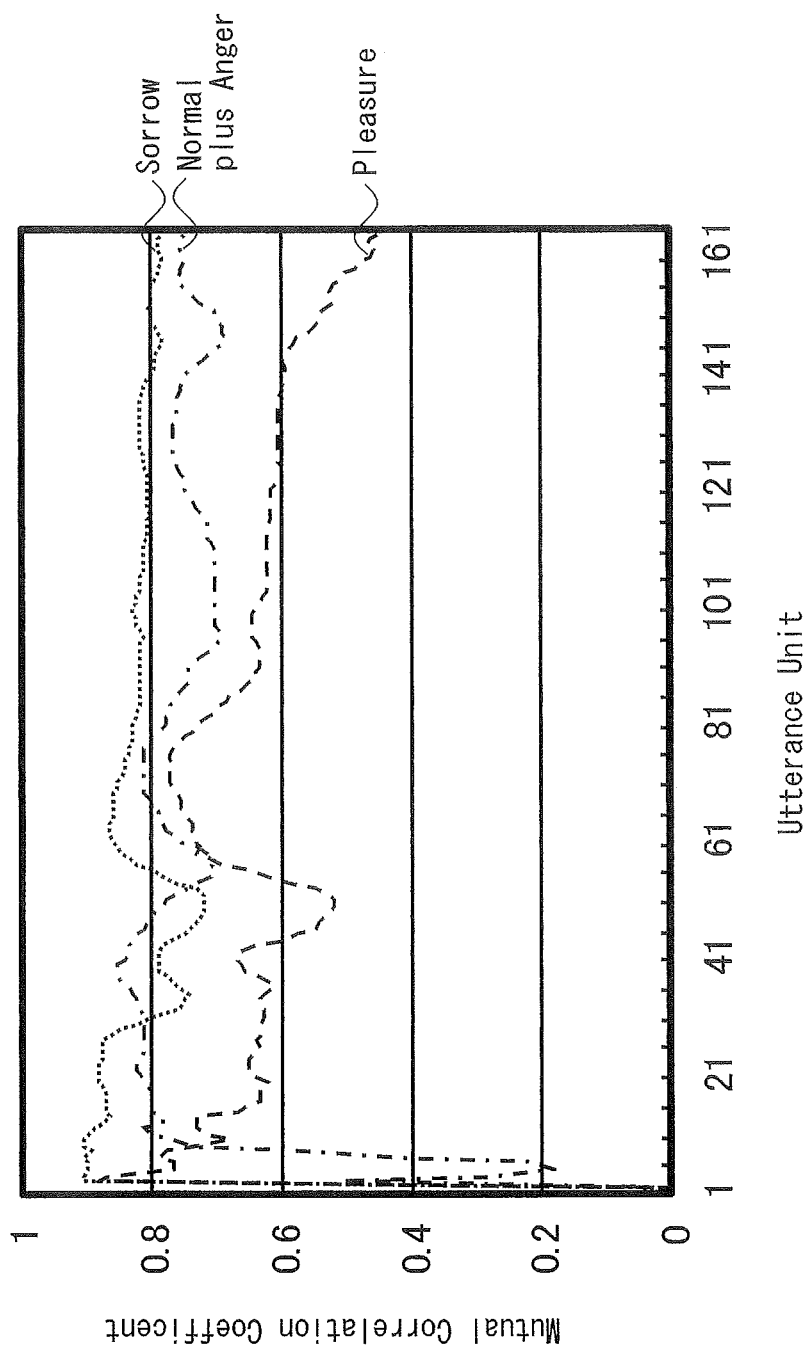
FIG. 9 is a diagram illustrating an example of results of a mutual correlation process between the degree of excitement and each emotion of the melancholiac illustrated in FIG. 5 which is performed by the calculation unit illustrated in FIG. 2.

FIG. 9 illustrates a change over time in a mutual correlation coefficient between an excitement degree of the melancholiac illustrated in FIG. 5 and the intensity of each of normal plus anger, sorrow, and pleasure. In the melancholiac illustrated in FIG. 9, a mutual correlation coefficient of sorrow has the largest, and a mutual correlation coefficient of pleasure has the smallest value in a 100 utterance unit and the subsequent utterance units. Meanwhile, similarly to the case of FIG. 8, in FIG. 9, a value of a mutual correlation coefficient between the excitement degree calculated by the calculation unit 20 and each emotion is not stabilized between the start of utterance and the 100 utterance unit, and thus the reliability of a result is low. For this reason, in the following description, mutual correlation coefficients in the 100 utterance unit and the subsequent utterance units are used in the case of the melancholiac illustrated in FIG. 9.

Figure 10:
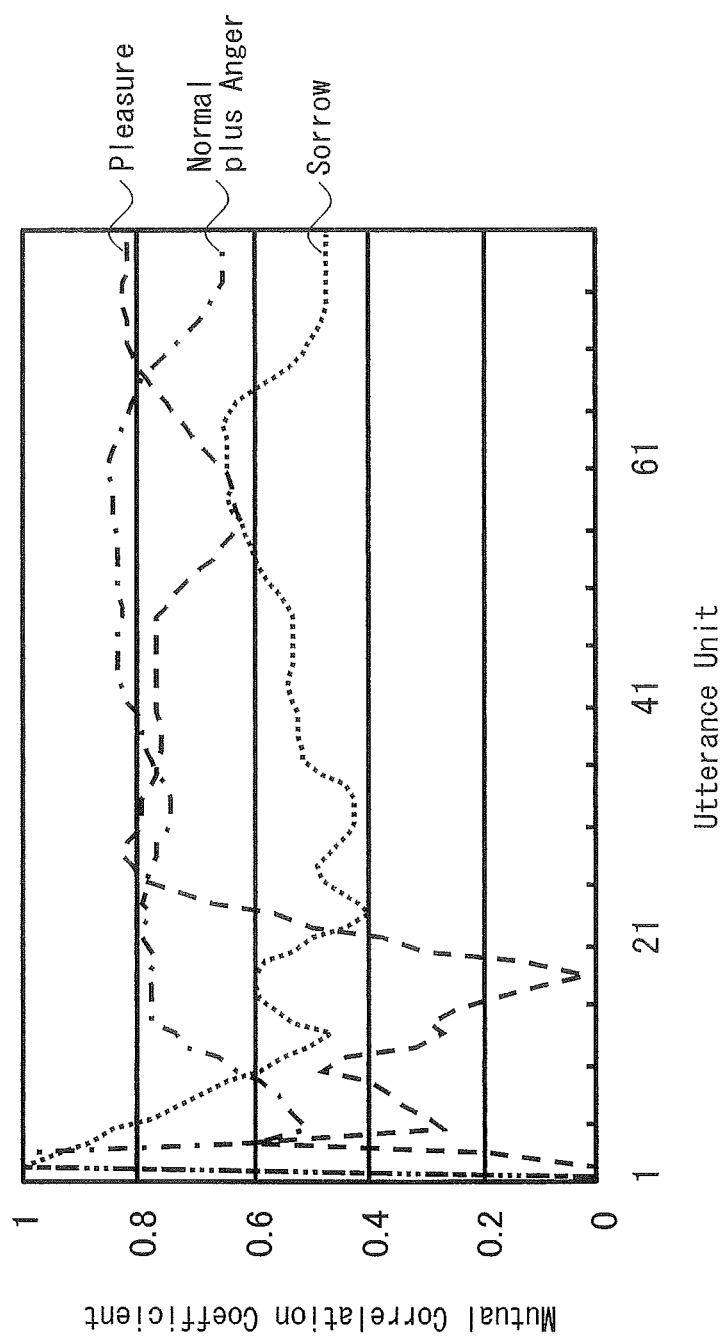
FIG. 10 is a diagram illustrating an example of results of a mutual correlation process between the degree of excitement and each emotion of the ordinary person illustrated in FIG. 6 which is performed by the calculation unit illustrated in FIG. 2.

FIG. 10 illustrates a change over time in a mutual correlation coefficient between an excitement degree of the ordinary person A illustrated in FIG. 6 and the intensity of each of normal plus anger, sorrow, and pleasure. In the ordinary person A illustrated in FIG. 10, a mutual correlation coefficient of pleasure has the largest value, and a mutual correlation coefficient of sorrow has the smallest value in a 70 utterance unit and the subsequent utterance units. Meanwhile, similarly to the cases of FIGS. 8 and 9, in FIG. 10, a value of a mutual correlation coefficient between the excitement degree calculated by the calculation unit 20 and each emotion is not stabilized between the start of utterance and the 70 utterance unit, and thus the reliability of a result is low. For this reason, in the following description, mutual correlation coefficients in the 70 utterance unit and the subsequent utterance units are used in the case of the ordinary person A illustrated in FIG. 10.

Figure 11:
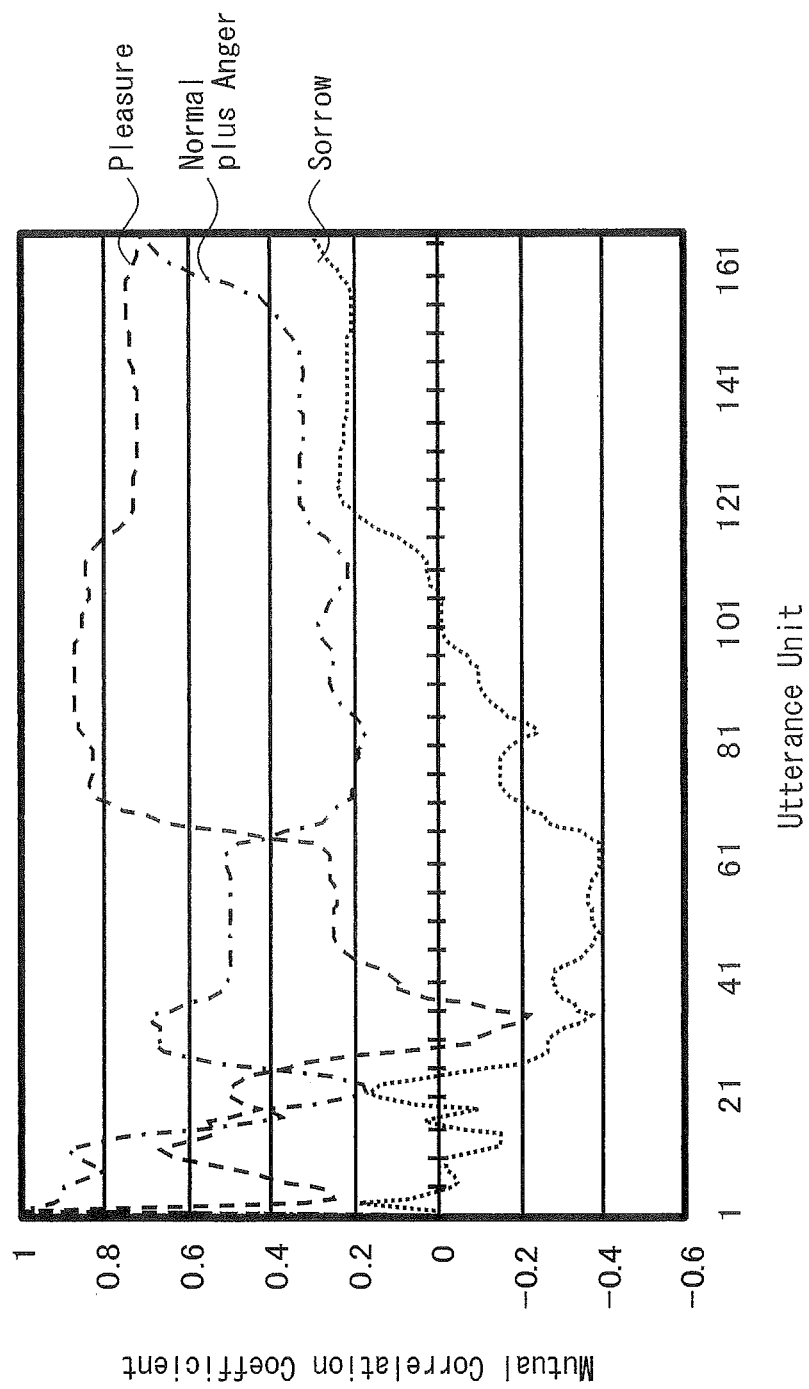
FIG. 11 is a diagram illustrating an example of results of a mutual correlation process between the degree of excitement and each emotion of the ordinary person illustrated in FIG. 7 which is performed by the calculation unit illustrated in FIG. 2.

FIG. 11 illustrates a change over time in a mutual correlation coefficient between an excitement degree of the ordinary person B illustrated in FIG. 7 and the intensity of each of normal plus anger, sorrow, and pleasure. In the ordinary person B illustrated in FIG. 11, a mutual correlation coefficient of pleasure has the largest value, and a mutual correlation coefficient of sorrow has the smallest value in a 70 utterance unit and the subsequent utterance units. Meanwhile, similarly to the cases of FIGS. 8 to 10, in FIG. 11, since the reliability of a calculation result of a mutual correlation coefficient between the excitement degree calculated by the calculation unit 20 and each emotion is low between the start of utterance and the 70 utterance unit, and thus mutual correlation coefficients in the 70 utterance unit and the subsequent utterance units are used in the case of the ordinary person B.

As illustrated in FIGS. 8 to 11, when subject PA are healthy people of the doctor, the ordinary person A, and the ordinary person B, an emotion of normal plus anger or pleasure has the highest correlation with an excitement degree, and an emotion of sorrow has the lowest correlation with an excitement degree. That is, it is considered that the healthy subject PA is in a mental state where the subject can genuinely show emotions together with a surge of excitement. In addition, such a mental state is a relatively primeval emotional state such as anger in many cases. On the other hand, when a subject PA is a melancholiac, an emotion of sorrow has the highest correlation with an excitement degree, and an emotion of pleasure has the lowest correlation with an excitement degree. That is, it is considered that even when the subject PA who is a melancholiac is in an excitement state, the subject, by contrast, is in a mental state of freezing from the bottom of his or her heart.

The calculation unit 20 obtains a balanced state between emotions of normal plus anger, sorrow, and pleasure of a subject PA, for example, using mutual correlation coefficients between an excitement degree of each of the subjects PA illustrated in FIGS. 8 to 11 and the intensity of each of normal plus anger, sorrow, and pleasure. That is, a living body such as a human body has a property of attempting to keep a physiological state and a mental state in a predetermined state in the entire living body regardless of a change in an internal or external environmental factor, and thus the calculation unit 20 obtains a balanced state between emotions. Meanwhile, the property of attempting to keep in a predetermined state in the entire living body is referred to as "constancy" or "homeostasis".

Figure 12:
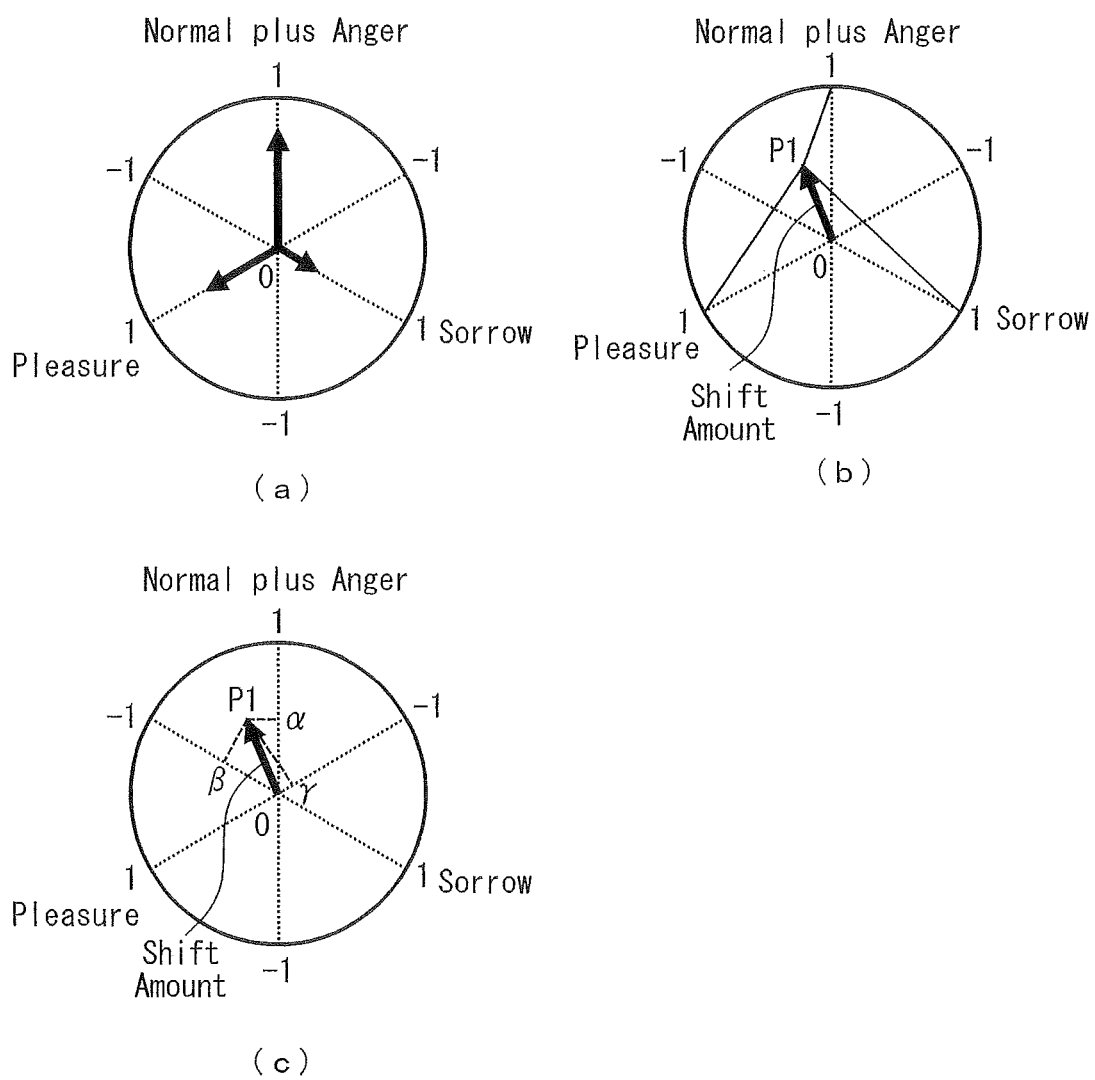
FIG. 12 is a diagram illustrating an example of the homeostasis of an emotion in a subject.

FIG. 12 illustrates an example of the homeostasis of an emotion of a subject PA. For example, FIG. 12(a) illustrates a coordinate system in which coordinate axes indicating respective emotions of normal plus anger, sorrow, and pleasure cross each other at an angle of 120 degrees. For example, as illustrated in FIGS. 8 to 11, in FIG. 12(a), mutual correlation coefficients of normal plus anger, sorrow, and pleasure which are obtained by the calculation unit 20 are indicated by vectors in the respective coordinate directions as intensities of the respective emotions of the subject PA. The calculation unit 20 obtains a balance between the emotions from the vectors of the respective emotions illustrated in FIG. 12(a). Meanwhile, a range of the intensities of the respective emotions of normal plus anger, sorrow, and pleasure is equal to a range of the mutual correlation coefficients, and is a range of −1 to 1.

FIG. 12(b) illustrates a balanced position P1 at which each emotion of the subject PA is balanced, which is obtained by the calculation unit 20, when the intensities of normal plus anger, sorrow, and pleasure of the subject PA are the vectors illustrated in FIG. 12(a). As illustrated in FIG. 12(b), the obtained balanced position P1 of the emotion of the subject PA is shifted from the center of the coordinate system. Consequently, the calculation unit 20 obtains a distance between the center of the coordinate system and the balanced position P1 of the emotion of the subject PA, as a shift amount of homeostasis. For example, as illustrated in FIG. 12(c), the calculation unit 20 obtains a shift amount of homeostasis as values α, β, and γ in the respective coordinate axes of normal plus anger, sorrow, and pleasure. In this manner, the calculation unit 20 can more increase the speed of an arithmetic process by obtaining a shift amount of homeostasis of the subject PA using the obtained mutual correlation coefficients of the respective emotions as vector components than when a shift amount of homeostasis is calculated using, for example, differentiation, integration, or the like.

FIGS. 13 to 16 illustrate examples of changes over time in shift amounts $\alpha$, $\beta$, and $\gamma$ of homeostasis in respective subjects PA which are obtained by the calculation unit 20 illustrated in FIG. 2. The vertical axis in each of FIGS. 13 to 16 represents a shift amount of each emotion, and the horizontal axis in each of FIGS. 13 to 16 represents the order of utterance units of a subject PA as a time axis. In addition, a dashed line represents a change over time in the shift amount $\alpha$ in a coordinate axis direction of normal plus anger, a dotted line represents a change over time in the shift amount $\beta$ in a coordinate axis direction of sorrow, and a broken line represents a change over time in the shift amount $\gamma$ in a coordinate axis direction of pleasure.

Figure 13:
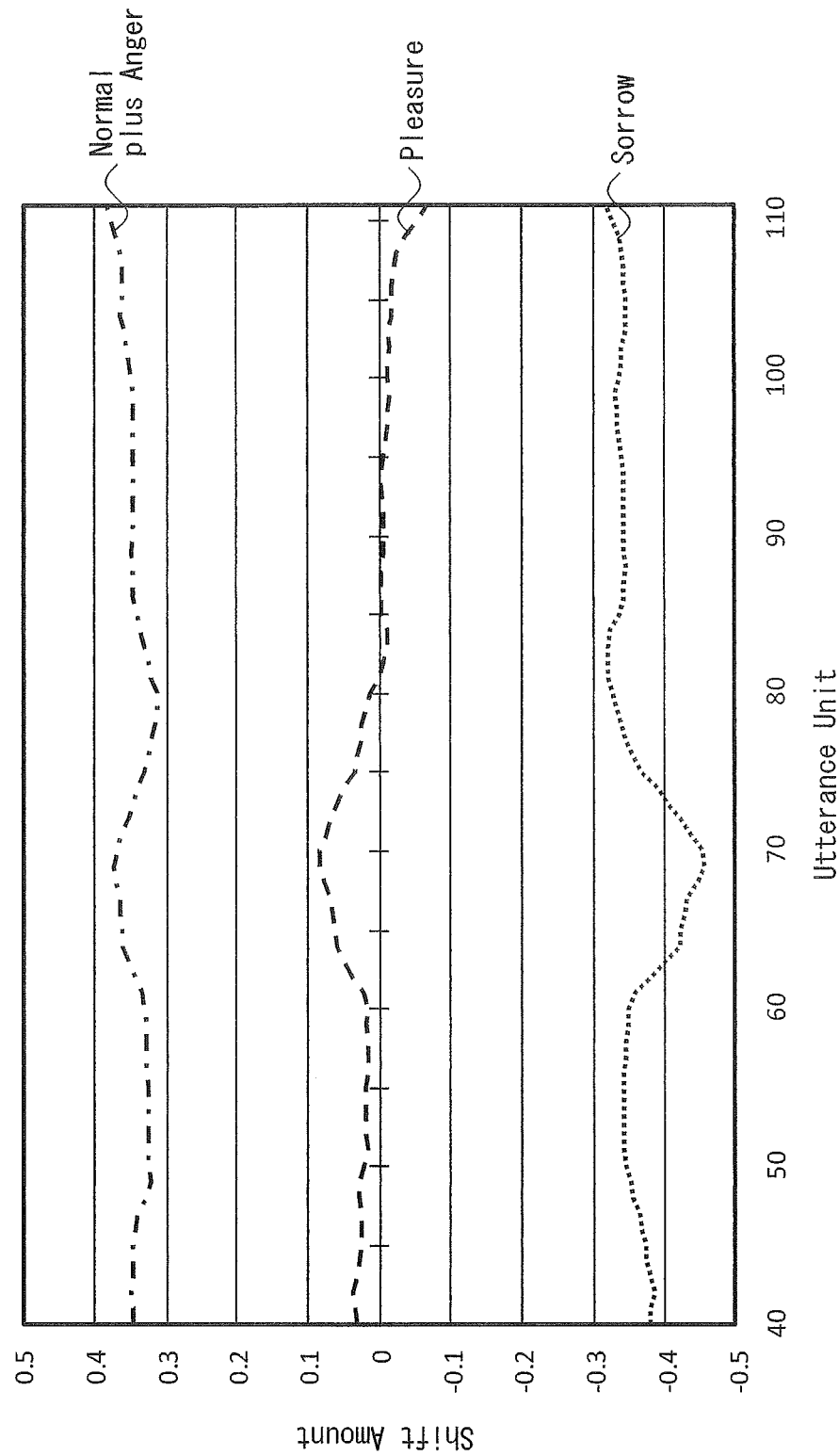
FIG. 13 is a diagram illustrating an example of a change over time in a shift amount of homeostasis in the doctor illustrated in FIG. 8 which is obtained by the calculation unit illustrated in FIG. 2.

FIG. 13 illustrates a change over time in a shift amount of homeostasis of an emotion of the doctor illustrated in FIG. 8. Meanwhile, FIG. 13 illustrates changes over time in the shift amounts $\alpha$, $\beta$, and $\gamma$ in a 40 utterance and the subsequent utterances in which a mutual correlation coefficient between an excitement degree and each emotion is stabilized. As illustrated in FIG. 13, the shift amount $\alpha$ of normal plus anger of the doctor has a positive value which is larger than the values of the shift amounts $\beta$ and $\gamma$ of sorrow and pleasure. In addition, the shift amount $\beta$ of sorrow of the doctor has a negative value which is smaller than that of the shift amount $\gamma$ of pleasure.

Figure 14:
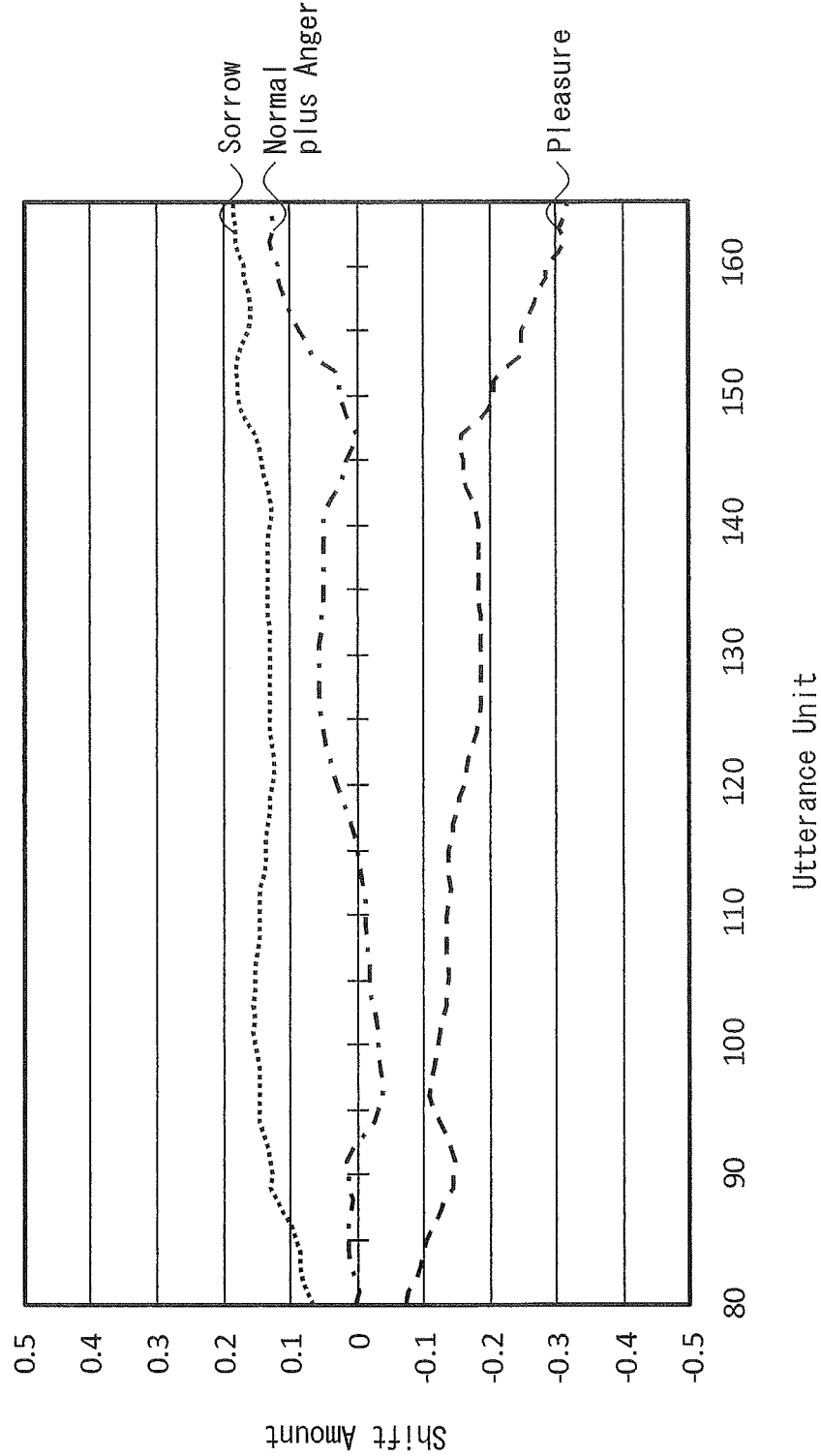
FIG. 14 is a diagram illustrating an example of a change over time in a shift amount of homeostasis in the melancholiac illustrated in FIG. 9 which is obtained by the calculation unit illustrated in FIG. 2.

FIG. 14 illustrates a change over time in a shift amount of homeostasis of an emotion of the melancholiac illustrated in FIG. 9. Meanwhile, FIG. 14 illustrates changes over time in the shift amounts $\alpha$, $\beta$, and $\gamma$ in a 100 utterance and the subsequent utterances in which a mutual correlation coefficient between an excitement degree and each emotion is stabilized. As illustrated in FIG. 14, the shift amount $\beta$ of sorrow of the melancholiac has a positive value which is larger than the values of the shift amounts $\alpha$ and $\gamma$ of normal plus anger and pleasure. In addition, the shift amount $\gamma$ of pleasure of the melancholiac has a negative value which is smaller than that of the shift amount $\alpha$ of normal plus anger.

Figure 15:
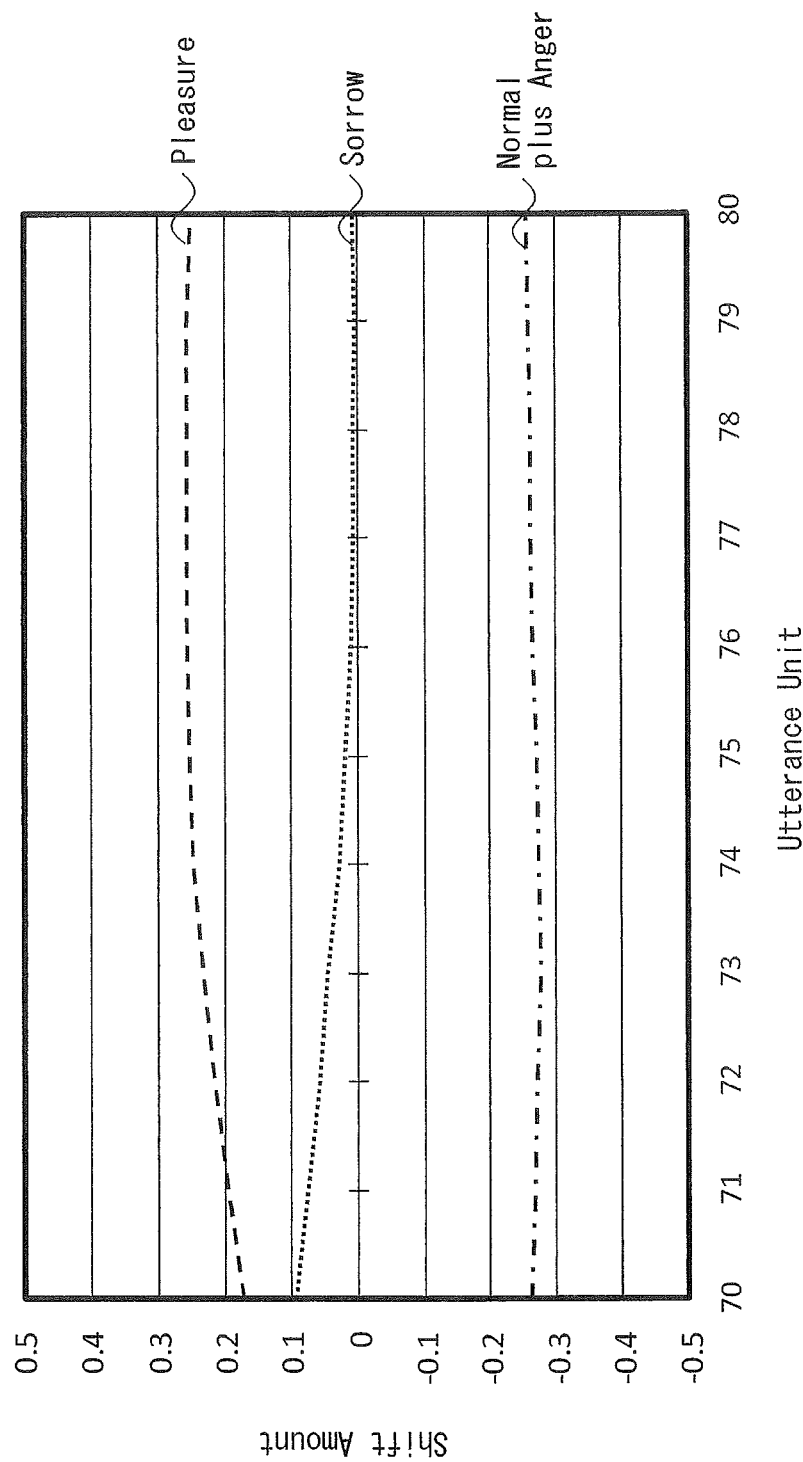
FIG. 15 is a diagram illustrating an example of a change over time in a shift amount of homeostasis in the ordinary person illustrated in FIG. 10 which is obtained by the calculation unit illustrated in FIG. 2.

FIG. 15 illustrates a change over time in a shift amount of homeostasis of an emotion of the ordinary person A illustrated in FIG. 10. Meanwhile, FIG. 15 illustrates changes over time in the shift amounts $\alpha$, $\beta$, and $\gamma$ in a 70 utterance and the subsequent utterances in which a mutual correlation coefficient between an excitement degree and each emotion is stabilized. In the ordinary person A illustrated in FIG. 15, the shift amount $\gamma$ of pleasure has a positive value which is larger than the values of the shift amounts $\alpha$ and $\beta$ of normal plus anger and sorrow. In addition, the shift amount $\beta$ of sorrow of the ordinary person A has a negative value which is smaller than that of the shift amount $\alpha$ of normal plus anger.

Figure 16:
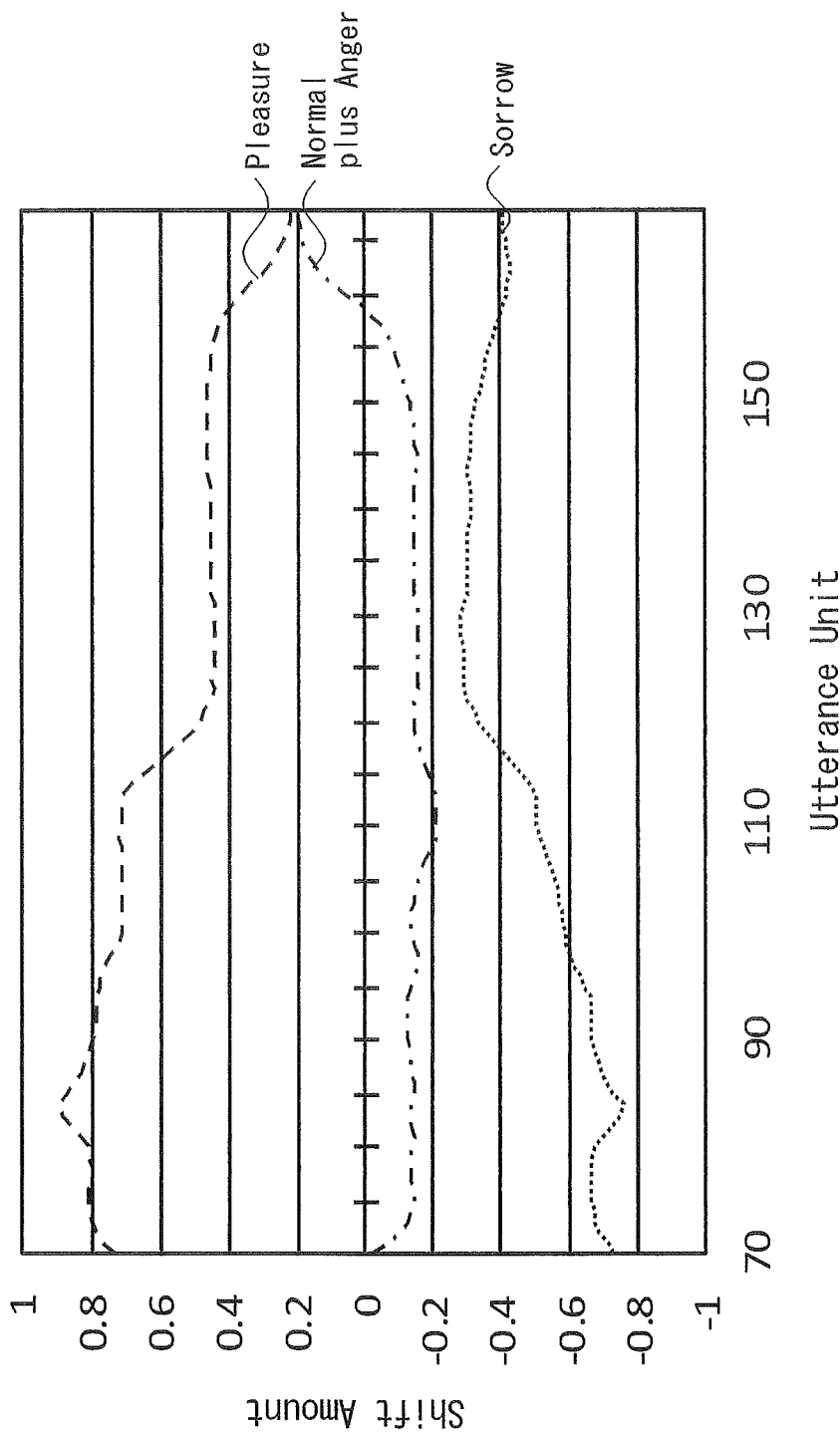
FIG. 16 is a diagram illustrating an example of a change over time in a shift amount of homeostasis in the ordinary person illustrated in FIG. 11 which is obtained by the calculation unit illustrated in FIG. 2.

FIG. 16 illustrates a change over time in a shift amount of homeostasis of an emotion of the ordinary person B illustrated in FIG. 11. Meanwhile, FIG. 16 illustrates changes over time in the shift amounts $\alpha$, $\beta$, and $\gamma$ in a 70 utterance and the subsequent utterances in which a mutual correlation coefficient between an excitement degree and each emotion is stabilized. In the ordinary person B illustrated in FIG. 16, the shift amount $\gamma$ of pleasure has a positive value which is larger than the values of the shift amounts $\alpha$ and $\beta$ of normal plus anger and sorrow, similar to the case of the ordinary person A illustrated in FIG. 15. In addition, the shift amount $\beta$ of sorrow of the ordinary person B has a negative value which is smaller than that of the shift amount $\alpha$ of normal plus anger.

The estimation unit 30 obtains a distance between the center of coordinates and the balanced position P1 illustrated in FIG. 12(b) based on, for example, the shift amounts of homeostasis illustrated in FIGS. 12 to 16. The estimation unit 30 estimates the pathology of a subject PA based on a distance between each of the shift amounts $\alpha$, $\beta$, and $\gamma$ and the obtained balanced position P1. For example, as in the doctor illustrated in FIG. 13, when the shift amount $\alpha$ of normal plus anger has a positive value, the shift amount $\beta$ of sorrow has a negative value which is smaller than the values of the shift amounts $\alpha$ and $\gamma$, and a distance from the balanced position P1 has a value equal to or less than a predetermined value, the estimation unit 30 estimates that the subject PA is healthy (or normal). However, when the distance from the balanced position P1 has a value larger than the predetermined value regardless of the shift amount $\alpha$ of normal plus anger having a positive value and the shift amount $\beta$ of sorrow having a negative value which is smaller than the values of the shift amounts $\alpha$ and $\gamma$, the estimation unit 30 estimates the subject PA is in a manic state.

In addition, for example, as in the ordinary person B illustrated in FIG. 16, when the shift amount $\gamma$ of pleasure has a positive value, the shift amount $\beta$ of sorrow has a negative value which is smaller than the values of the shift amounts $\alpha$ and $\gamma$, and a distance from the balanced position P1 has a value equal to or less than a predetermined value, the estimation unit 30 estimates that the subject PA is healthy (or normal). However, when the distance from the balanced position P1 has a value larger than the predetermined value regardless of the shift amount $\gamma$ of pleasure having a positive value and the shift amount $\beta$ of sorrow having a negative value which is smaller than the values of the shift amounts $\alpha$ and $\gamma$, the estimation unit 30 estimates that the subject PA is in a manic state. On the other hand, for example, as in the melancholiac illustrated in FIG. 14, when the shift amount $\beta$ of sorrow has a positive value which is larger than the values of the shift amounts $\alpha$ and $\gamma$ of normal plus anger and pleasure, the estimation unit 30 estimates that the subject PA is in a depression state.

Meanwhile, a magnitude relation between shift amounts $\alpha$, $\beta$, and $\gamma$ and a relationship between a predetermined value with respect to a distance from the balanced position P1 and pathology may be determined based on, for example, International Statistical Classification of Diseases and Related Health Problems 10th revision (ICD-10) or the like. The determined magnitude relation between the shift amounts $\alpha$, $\beta$, and $\gamma$ and relationship between a predetermined value with respect to a distance from the balanced position P1 and pathology are stored in the storage device of the estimation device 100 in advance. Here, ICD is an abbreviation of international statistical classification of diseases and related health problems. In addition, the predetermined value may be adjusted in consideration of differences between individual subjects PA.

In addition, the estimation unit 30 may determine the pathology of a subject PA in detail in consideration of a distance between each of shift amounts $\alpha$, $\beta$, and $\gamma$ and the balanced position P1 and a direction in which the balanced position P1 is shifted with respect to the center of coordinates, or the like. In addition, the estimation unit 30 may estimate the pathology of the subject PA based on the shift amounts $\alpha$, $\beta$, and $\gamma$. Alternatively, the estimation unit 30 may estimate the pathology of the subject PA based on, for example, the immobilization of deviations indicated by the shift amounts α, β, and γ of homeostasis in the subject PA and the speed of a change.

In addition, the estimation unit 30 may estimate the pathology of the subject PA using the shift amounts α, β, and γ which are calculated by the calculation unit 20 for a long period of time such as two weeks. The estimation unit 30 can estimate the pathology of the subject PA with a high level of accuracy by using data of shift amounts for a long period of time.

Figure 17:
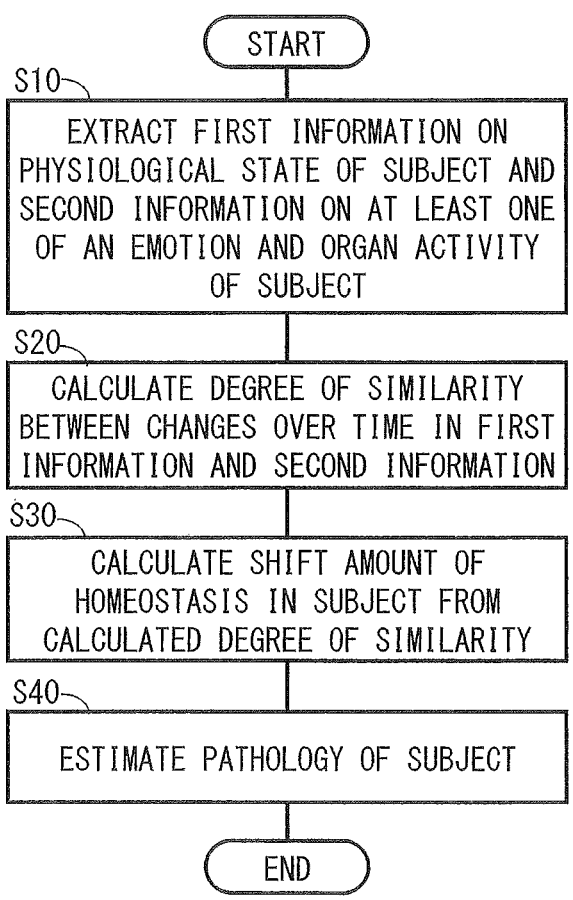
FIG. 17 is a diagram illustrating an example of an estimation process which is performed by the estimation device illustrated in FIG. 2.

FIG. 17 illustrates an example of an estimation process performed by the estimation device 100 illustrated in FIG. 2. Steps S10 to S40 are performed by a CPU, mounted on the estimation device 100, executing an estimation program. That is, FIG. 17 illustrates a program and an estimation method according to another embodiment. In this case, the extraction unit 10, the calculation unit 20, and the estimation unit 30 illustrated in FIG. 2 are realized by the execution of the program. Meanwhile, the process illustrated in FIG. 17 may be realized by hardware mounted on the estimation device 100. In this case, the extraction unit 10, the calculation unit 20, and the estimation unit 30 illustrated in FIG. 2 are realized by circuits disposed within the estimation device 100.

In step S10, as described in FIGS. 2 to 7, the extraction unit 10 extracts first information indicating a physiological state of a subject PA and second information indicating at least one of an emotion and organ activity based on information indicating the physiology of the subject PA which is measured by the measurement device 1.

In step S20, as described in FIGS. 4 to 11, the calculation unit 20 performs a mutual correlation process on changes over time in the first information and the second information which are extracted, to thereby calculate a mutual correlation coefficient indicating the degree of similarity.

In step S30, as described in FIGS. 12 to 16, the calculation unit 20 obtains a shift amount of homeostasis in the subject PA based on the obtained mutual correlation coefficient.

In step S40, as described in FIGS. 12 to 16, the estimation unit 30 estimates the pathology of the subject PA based on the shift amount of homeostasis in the subject PA which is obtained by the calculation unit 20.

In addition, the estimation process performed by the estimation device 100 is terminated. A flow illustrated in FIG. 17 may be repeatedly performed whenever an instruction is given from a doctor or a subject PA, or may be performed at a predetermined frequency. In addition, the estimation device 100 outputs an estimation result to the output device 2. The output device 2 displays a result of the estimated pathology and a shift amount of homeostasis. In addition, the output device 2 may represent the magnitude of a shift amount of homeostasis, that is, the degree of a symptom of the estimated pathology or a degree indicating the health of the subject PA by a color or a facial expression of a person, an animal, or the like of an animation, and may display the magnitude on a display. In addition, the output device 2 may display an advice such as a method for treatment of the estimated pathology in accordance with the magnitude of a shift amount of homeostasis.

As described above, in the embodiment illustrated in FIGS. 2 to 17, a shift amount of homeostasis in a subject PA is calculated using first information indicating a physiological state of the subject PA and second information indicating at least one of an emotion and organ activity of the subject PA. Thereby, the estimation device 100 can easily estimate the pathology of the subject PA without having expert knowledge on medicine with reference to an index such as a shift amount of the homeostasis.

Meanwhile, the calculation unit 20 may obtain intensities of emotions of normal, sorrow, anger, and pleasure of a subject PA using, for example, a determination tree indicating a relationship between a heart rate, a heartbeat fluctuation, and an emotion, instead of using the determination tree indicating a relationship between a fundamental frequency of utterance and an emotion which is illustrated in FIG. 3.

Figure 18:
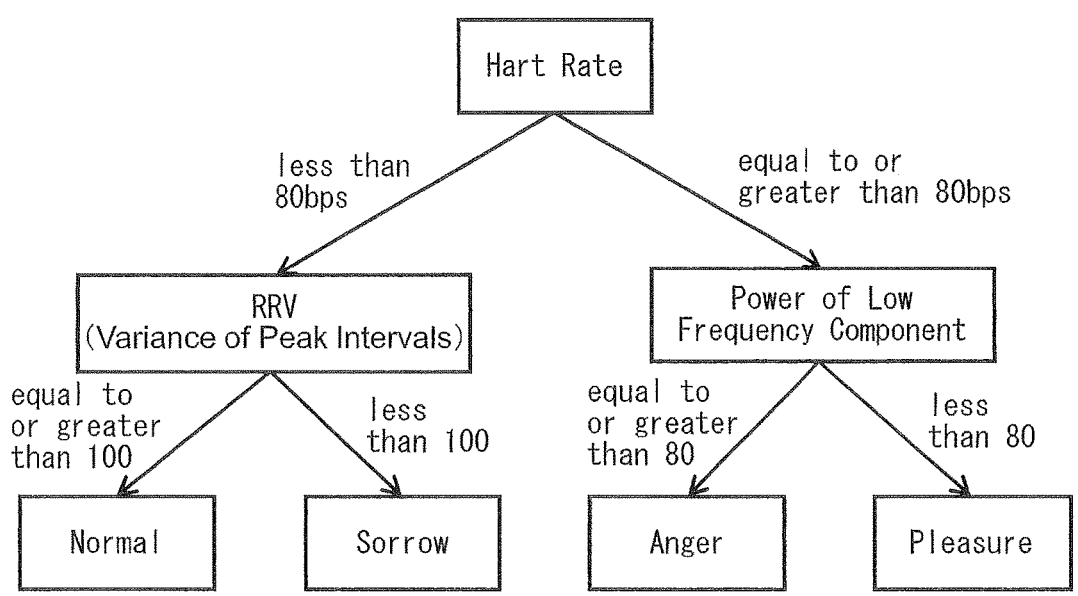
FIG. 18 is a diagram illustrating an example of a determination tree of a subject's heart rate and heartbeat fluctuation and the subject's emotion.

FIG. 18 illustrates an example of a determination tree indicating a heart rate and heartbeat fluctuation of a subject PA and an emotion of the subject PA. Meanwhile, R-R Variance (RRV) illustrates variance of an interval between R waves in an electrocardiogram. As illustrated in FIG. 18, for example, an emotion of normal is defined as a case where a heart rate is less than 80 bps and RRV is equal to or greater than 100. In addition, an emotion of sorrow is defined as a case where a heart rate is less than 80 bps and RRV is less than 100. An emotion of anger is defined as a case where a heart rate is equal to or greater than 80 bps and a power of a low frequency component LF of a heartbeat fluctuation is equal to or greater than 80. An emotion of pleasure is defined as a case where a heart rate is equal to or greater than 80 bps and a power of a low frequency component LF is less than 80.

In addition, as illustrated in FIG. 12(c), the calculation unit 20 obtains shift amounts α, β, and γ of homeostasis in a subject PA, but may obtain shift amounts α, β, and γ, for example, as illustrated in FIG. 19.

FIG. 19 illustrates another example of homeostasis of an emotion of a subject PA. A coefficient h illustrated in FIG. 19 is an index indicating which of a shift amount γ of pleasure in a coordinate axis direction and a shift amount β of sorrow in a coordinate axis direction is larger in a vector V1 directed to a balanced position P1 from the center of a coordinate system. That is, the coefficient h has a positive value when the shift amount γ of pleasure is larger than the shift amount β of sorrow, and has a negative value when the shift amount β of sorrow is larger than the shift amount γ of pleasure. In addition, when the shift amount γ of pleasure and the shift amount β of sorrow contend with each other, the coefficient h is set to 0.

For example, the calculation unit 20 obtains an angle θ formed by the vector V1 and the coordinate axis of pleasure in order to obtain the coefficient h. Meanwhile, when the shift amount γ of pleasure is larger than the shift amount β of sorrow, the angle θ has a small value which is close to 0 degrees (that is, the direction of the vector V1 is the coordinate axis direction of pleasure). On the other hand, when the shift amount β of sorrow is larger than the shift amount γ of pleasure, the angle θ has a large value in which the direction of the vector V1 is close to the coordinate axis direction of sorrow. As illustrated in FIG. 19, the calculation unit 20 obtains the coefficient h using the obtained angle θ and a length L of the vector V1 in accordance with a case where the balanced position P1 is in a region (hereinafter, a region A) between pleasure and sorrow (counterclockwise) and a case where the balanced position is in a region (hereinafter, a region B) between pleasure and sorrow (clockwise). In addition, the calculation unit 20 sets the obtained coefficient h to the shift amount γ of pleasure of the vector V1 and sets a negative coefficient h to the shift amount β of sorrow. That is, the relation of β+γ=0 is established.

In addition, in the case of the region A illustrated in (a) of FIG. 19, when the coefficient h has a value close to 0 (that is, the angle θ is π/3), the direction of the vector V1 is set to be a negative direction of a coordinate axis of normal plus anger. That is, the shift amount γ of pleasure and the shift amount β of sorrow contend with each other and are larger than the shift amount α of normal plus anger. In other words, the shift amount α of normal plus anger is smaller than the shift amount γ of pleasure and the shift amount β of sorrow. Consequently, when the vector V1 is in the region A, the calculation unit 20 obtains |h|−L as the shift amount α of normal plus anger. On the other hand, in the case of the region B illustrated in (b) of FIG. 19, when the coefficient h has a value close to 0 (that is, the angle θ is 2 π/3), the direction of the vector V1 is set to be a positive direction of a coordinate axis of normal plus anger. That is, the shift amount γ of pleasure and the shift amount β of sorrow contend with each other and are smaller than the shift amount α of normal plus anger. In other words, the shift amount α of normal plus anger is larger than the shift amount γ of pleasure and the shift amount β of sorrow. Consequently, when the vector V1 is in the region B, the calculation unit 20 obtains L−|h| as the shift amount α of normal plus anger. Thereby, the calculation unit 20 can calculate a positive shift amount α when the balanced position P1 is in the vicinity of the axis of positive normal plus anger, and can calculate a negative shift amount α when the balanced position P1 is in the vicinity of the axis of negative normal plus anger.

For example, when the shift amount β of sorrow has a positive value larger than 0 and the shift amounts α and γ of normal plus anger and pleasure have small values close to 0, the estimation unit 30 estimates that the subject PA is in a depression state using the shift amounts α, β, and γ illustrated in FIG. 19. In addition, when the shift amount γ of pleasure has a positive value larger than 0 and the shift amounts α and β of normal plus anger and sorrow have values close to 0, the estimation unit 30 estimates that the subject PA is in a manic state. In addition, when the shift amount α of a normal plus anger component has a value smaller than 0 (close to −1) and the shift amounts β and γ of sorrow and pleasure have the same value and contend with each other, the estimation unit 30 estimates that the subject PA is in a manic depression state.

Figure 20:
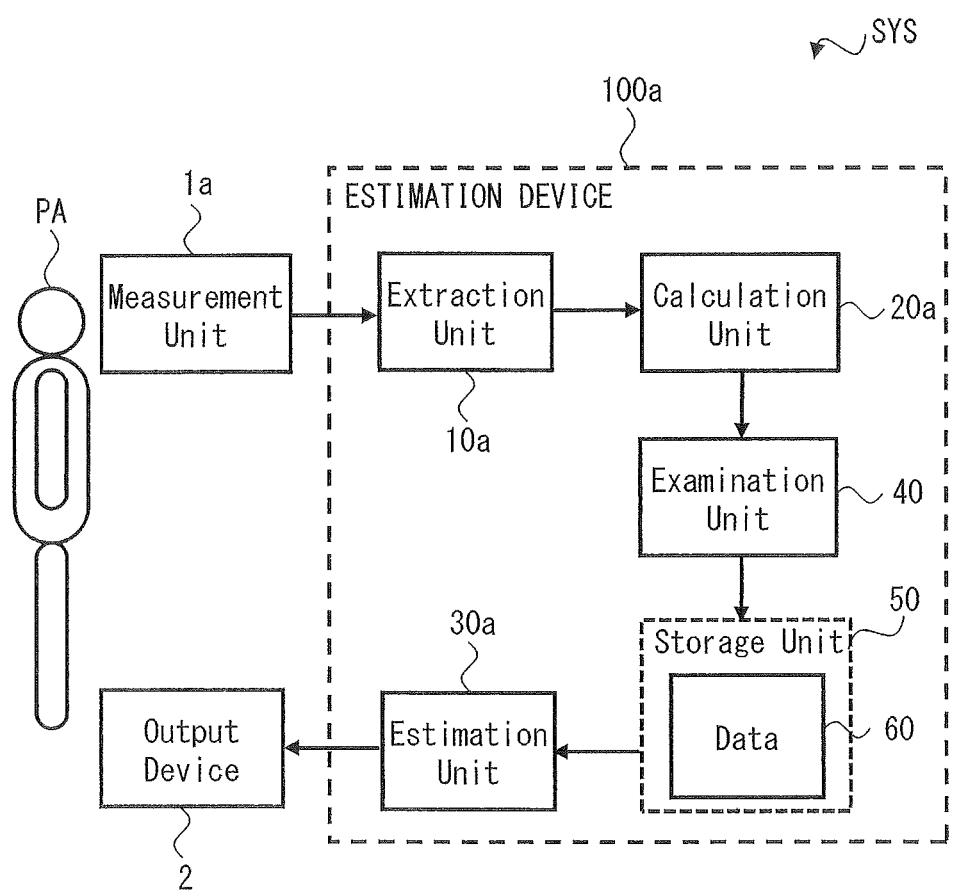
FIG. 20 is a diagram illustrating an estimation device according to still another embodiment.

FIG. 20 illustrates an estimation device and an estimation process according to another embodiment. Components having functions that are the same as or similar to those of the components described in FIG. 2 will be denoted by the same or similar reference numerals and signs, and a detailed description thereof will be omitted.

An estimation device 100a illustrated in FIG. 20 is a computer device or the like which includes an arithmetic processor such as a CPU and a storage device such as a hard disk device. The estimation device 100a is connected to a measurement device 1a and an output device 2 through an interface unit included in the estimation device 100a in a wired or wireless manner. Thereby, the estimation device 100a, the measurement device 1a, and the output device 2 operate as an estimation system SYS.

The measurement device 1a includes a plurality of devices such as a microphone, a heartbeat meter, an electrocardiograph, a hemopiezometer, a clinical thermometer, a skin resistance meter, a camera, and a Magnetic Resonance Imaging (MRI) device, and measures information indicating the physiology of a subject PA. The measurement device 1a outputs information indicating the measured physiology of the subject PA to the estimation device 100a. Meanwhile, the measurement device 1a may have an acceleration sensor, an electronic gyroscope, or the like.

The information indicating the physiology of a subject PA which is measured by the measurement device 1a includes a sound signal and, for example, a heart (pulse) rate, a heartbeat fluctuation, blood pressure, body temperature, the amount of perspiration (skin resistance, skin potential), the motion of an eyeball, a pupil diameter, and the number of winkings. Furthermore, the measured physiology information includes, for example, sighs, hormone, and secretions in the body such as biomolecules, brain waves, functional MRI (fMRI) information, and the like.

In addition, the estimation device 100a includes an extraction unit 10a, a calculation unit 20a, an estimation unit 30a, an examination unit 40, and a storage unit 50. Functions of the extraction unit 10a, the calculation unit 20a, the estimation unit 30a, and the examination unit 40 may be realized by a program executed by a CPU or may be realized by hardware.

The extraction unit 10a extracts first information indicating a physiological state of a subject PA from information indicating the physiology of the subject PA which is measured by the measurement device 1a, in a manner that is the same as or similar to the extraction unit 10 illustrated in FIG. 2. In addition, the extraction unit 10a extracts second information indicating at least one of an emotion of the subject PA and the activity of an organ such as the heart or bowel of the subject PA from information indicating the physiology of the subject PA which is measured by the measurement device 1a, in a manner that is the same as or similar to the extraction unit 10 illustrated in FIG. 2.

For example, the extraction unit 10a extracts a heart (pulse) rate measured by the heartbeat meter included in the measurement device 1a, or the like, as the second information indicating an emotion and organ activity of the subject PA. Meanwhile, there is a property that a heartbeat increases by an increase in the amount of adrenalin secreted in the body due to excitement or tension and a heart (pulse) rate increases.

In addition, for example, the extraction unit 10a performs frequency analysis such as FFT on an electrocardiographic waveform of a subject PA which is measured using the electrocardiograph included in the measurement device 1a to thereby acquire a heartbeat fluctuation of the subject PA. In addition, the extraction unit 10a compares the amount of low frequency components LF (for example, 0.04 hertz to 0.14 hertz) of the acquired heartbeat fluctuation with the amount of high frequency components HF (for example, 0.14 hertz to 0.5 hertz) to thereby extract the level of excitement or tension of the subject PA as the first information indicating the physiological state of the subject PA. Meanwhile, there is a property that the low frequency components LF of the heartbeat fluctuation increase mainly in association with the activity of sympathetic nerves and the high frequency components HF increase in association with the activity of parasympathetic nerves.

In addition, for example, the extraction unit 10a extracts a value of blood pressure measured using the hemopiezometer included in the measurement device 1a, as the second information indicating an emotion and organ activity of the subject PA. Meanwhile, with regard to the blood pressure, there is a property that when a blood vessel contracts in association with excitement or tension, resistance to the bloodstream increases, which leads to an increase in blood pressure.

In addition, for example, the extraction unit 10a extracts a value of body temperature measured using the clinical thermometer included in the measurement device 1a, or the like, as the second information indicating an emotion and organ activity of the subject PA. Meanwhile, with regard to the body temperature, there is a property that heat is generated in the body due to an increase in a heartbeat, an increase in a blood sugar level, the occurrence of muscular tension, and the like in association with excitement or tension, which leads to an increase in body temperature.

In addition, for example, the extraction unit 10a extracts a value of the amount of perspiration (skin resistance, skin potential) which is measured using the skin resistance meter included in the measurement device 1a, or the like, as the second information indicating an emotion and organ activity of the subject PA. Meanwhile, with regard to the amount of perspiration (skin resistance, skin potential), there is a property that perspiration is promoted due to excitement or tension, which leads to a decrease in skin resistance.

In addition, for example, the extraction unit 10a extracts the motion of an eyeball, a pupil diameter, and the number of times of winking which are measured using the eye electrometer or the camera of the measurement device 1a, or the like, as the second information indicating an emotion and organ activity of the subject PA. The extraction unit 10a may perform a face recognition process on an image captured using, for example, the camera to thereby extract a facial expression recognized and a change over time in the facial expression as the second information indicating an emotion and organ activity of the subject PA. Meanwhile, with regard to the motion of an eyeball, there is a property that the motion of an eyeball becomes intense due to excitement or tension. With regard to the pupil diameter, there is a property that a pupil is enlarged due to excitement or tension. With regard to the number of winkings, there is a property that the number of times of winking is increased due to excitement or tension.

In addition, for example, the extraction unit 10a extracts the number of sighs, speed, displacement, and the like which are measured from the amount of breathing and a breathing sound using a breathing meter (breathing flow meter), a spirometer, a microphone, or the like included in the measurement device 1a, as the second information indicating an emotion and organ activity of the subject PA. Meanwhile, with regard to the sigh, there is a property that the number of sighs, speed, and displacement are increased due to excitement or tension.

In addition, for example, the extraction unit 10a extracts each of hormone and secretions in the body such as biomolecules which are measured using an analysis device included in the measurement device 1a, as the second information indicating an emotion and organ activity of the subject PA. Meanwhile, the hormone and the secretions in the body such as biomolecules are measured by the analysis device of the measurement device 1a which performs chemical analysis of saliva, blood, lymph, sweat, digestive juices, urine, or the like which is taken from the subject PA. Alternatively, the secretions in the body may be measured by the measurement device 1a from a peripheral vessel, digestive system, muscle potential, skin temperature, blood flow rate, immune system, or the like of the subject PA. Meanwhile, with regard to the secretions in the body, there is a property that the amount or quality of hormone or biomolecules secreted in the body changes due to excitement or tension.

In addition, for example, the extraction unit 10a extracts a variation in brain waves with respect to time which is measured using a brain activity meter, such as an optical, magnetic, or potential type meter, included in the measurement device 1a, or the like, as the first information indicating excitement or tension of the subject PA. Meanwhile, with regard to the brain waves, there is a property that a waveform changes due to excitement or tension.

In addition, for example, the extraction unit 10a extracts a blood flow rate and distribution of oxygenated hemoglobin in each activity region in the brain which are included in fMRI information measured by the MRI device included in the measurement device 1a, as the second information indicating an emotion and organ activity of the subject PA. Meanwhile, with regard to the measured fMRI information, there is a property that an activity region in the brain changes due to excitement or tension. For example, excitement or tension related to an emotion appears as a change in a blood flow rate in a limbic system (amygdala), hypothalamus, cerebellum, brainstem, hippocampus, or the like. Such a change in a blood flow rate changes the distribution of oxygenated hemoglobin in the brain.

Meanwhile, when the measurement device 1a includes an acceleration sensor, an electronic gyro, or the like, the extraction unit 10a may extract the movement of a subject PA as the second information indicating an emotion and organ activity of the subject PA.

The calculation unit 20a calculates the degree of similarity between changes over time in the first information and the second information which are extracted by the extraction unit 10a. For example, the calculation unit 20a performs a mutual correlation process of the changes over time in the first information and the second information which are extracted, to thereby calculate a mutual correlation coefficient as the degree of similarity. The calculation unit 20a obtains a shift amount of homeostasis in a subject PA using the calculated plurality of degrees of similarity in an emotion and organ activity of the subject PA. The operation of the calculation unit 20a and homeostasis will be described with reference to FIG. 21.

The examination unit 40 calculates energy acting on an emotion and organ activity of a subject PA from the shift amount of homeostasis which is calculated by the calculation unit 20a. The examination unit 40 inputs the calculated energy to a calculation model indicating the living body of the subject PA to simulate homeostasis in the subject PA. The calculation model and the operation of the examination unit 40 will be described with reference to FIGS. 22 and 23.

The storage unit 50 is a hard disk device, a memory, or the like. The storage unit 50 stores a program executed by a CPU. In addition, the storage unit 50 stores data 60 indicating a result of the simulation performed by the examination unit 40. The data 60 will be described with reference to FIG. 23.

Meanwhile, a program for executing an estimation process can be recorded in a removable disc such as a compact disc (CD) or a digital versatile disc (DVD) and can be distributed. In addition, the estimation device 100a may download the program for executing an estimation process from a network through a network interface included in the estimation device 100a, and may store the downloaded program in the storage unit 50.

The estimation unit 30a estimates the pathology of a subject PA from a pattern of a change in the homeostasis simulated by the examination unit 40. The operation of the estimation unit 30a will be described with reference to FIGS. 22 and 23.

Figure 21:
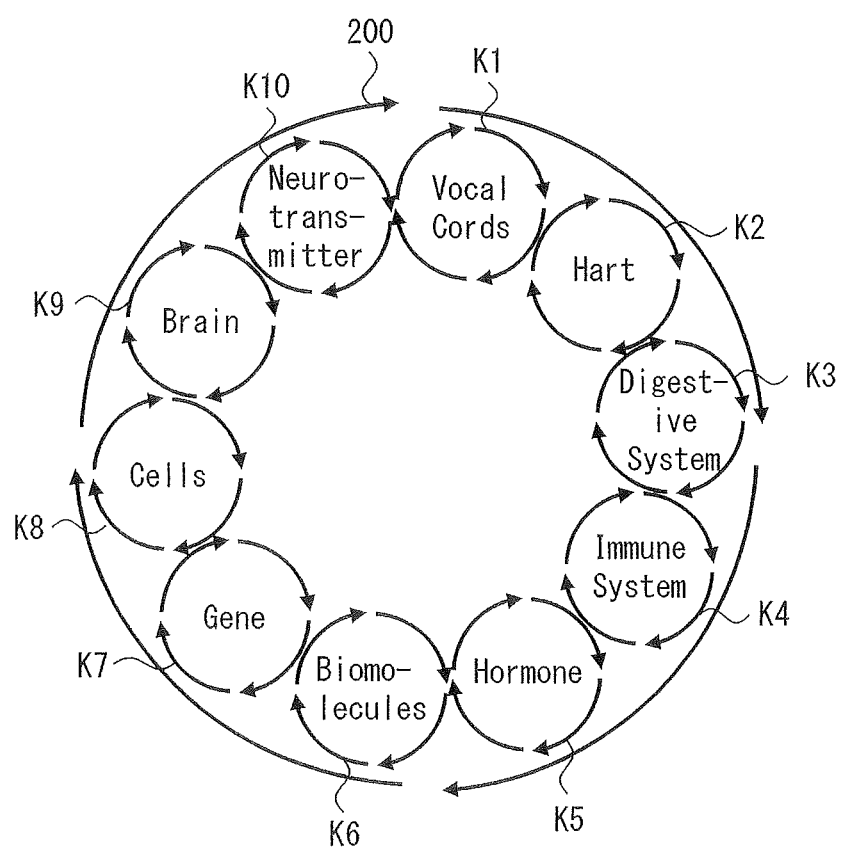
FIG. 21 is a schematic diagram illustrating an example of a chain of homeostasis in a subject PA.

FIG. 21 schematically illustrates an example of a chain of homeostasis in a subject PA. In FIG. 21, for example, a circulation system 200 is configured by representing a balance of homeostasis of the entire living body of the subject PA by the rotation of a circular figure. The circulation system 200 further includes, for example, a plurality of circulation systems K (K1 to K10) such as materials and organs forming the subject PA. In FIG. 21, the circulation systems K1 to K10 are represented by the rotation of circles that are linked together to maintain a balance of homeostasis and are smaller than the circulation system 200. For example, the circulation system K1 indicates the homeostasis of an emotion of the subject PA based on a sound signal uttered by the subject PA through the vocal cords. For example, the circulation system K2 indicates the homeostasis of the heart of the subject PA based on a heart rate, a heartbeat fluctuation, and the like. For example, the circulation system K3 indicates the homeostasis of the digestive system of the subject PA such as the stomach, the small intestine, or the large intestine. For example, the circulation system K4 indicates the homeostasis of the immune system that protects the subject PA from illness or the like. For example, the circulation system K5 indicates the homeostasis of hormone that transmits information for adjusting the movement of an organ included in the living body of the subject PA.

In addition, for example, the circulation system K6 indicates the homeostasis of biomolecules such as a plurality of types of protein generated by a gene of the subject PA. For example, the circulation system K7 indicates the homeostasis of a gene of the subject PA. For example, the circulation system K8 indicates the homeostasis of activity of cells forming the subject PA. For example, the circulation system K9 indicates the homeostasis of activity of the limbic system of the subject PA which includes amygdala and the like in the brain which is closely related to an emotion. For example, the circulation system K10 indicates the homeostasis of a neurotransmitter that mediates the transmission of information at synapses.

Meanwhile, the circulation system 200 is configured to include ten circulation systems K1 to K10, but is not limited thereto. The circulation system may include any number of plurality of circulation systems other than ten. In addition, each of the circulation systems K may further include a plurality of circulation systems. For example, the circulation system K1 of the vocal cords may include a plurality of circulation systems indicating emotions such as anger, normal, sorrow, and pleasure of a subject PA. In addition, for example, the circulation system K2 of the heart may include a plurality of circulation systems indicating a heart rate, a heartbeat fluctuation, and the like of a subject PA.

For example, for example, as described in FIG. 12, the calculation unit 20a obtains a shift amount of homeostasis in each of the circulation systems K of a subject PA using the calculated plurality of degrees of similarity in an emotion and organ activity of the subject PA. For example, similarly to the calculation unit 20 illustrated in FIG. 2, the calculation unit 20a calculates a shift amount of homeostasis of an emotion of the subject PA based on a sound signal of the subject PA. In addition, for example, the calculation unit 20a performs a mutual correlation process on changes over time in the excitement degree or tension which is obtained from a ratio of a low frequency component LF to a high frequency component HF of a heartbeat fluctuation which are measured by an electrocardiograph, a heart rate, blood pressure, and the like. In addition, for example, the calculation unit 20a calculates a shift amount of homeostasis of the heart of the subject PA from a change over time in a mutual correlation coefficient between the excitement degree or tension and each of a heart rate, blood pressure, and the like.

Meanwhile, the calculation unit 20a calculates a shift amount of homeostasis in each of all of the circulation systems K1 to K10, but a shift amount of homeostasis in some of the circulation systems K may be calculated.

Figure 22:
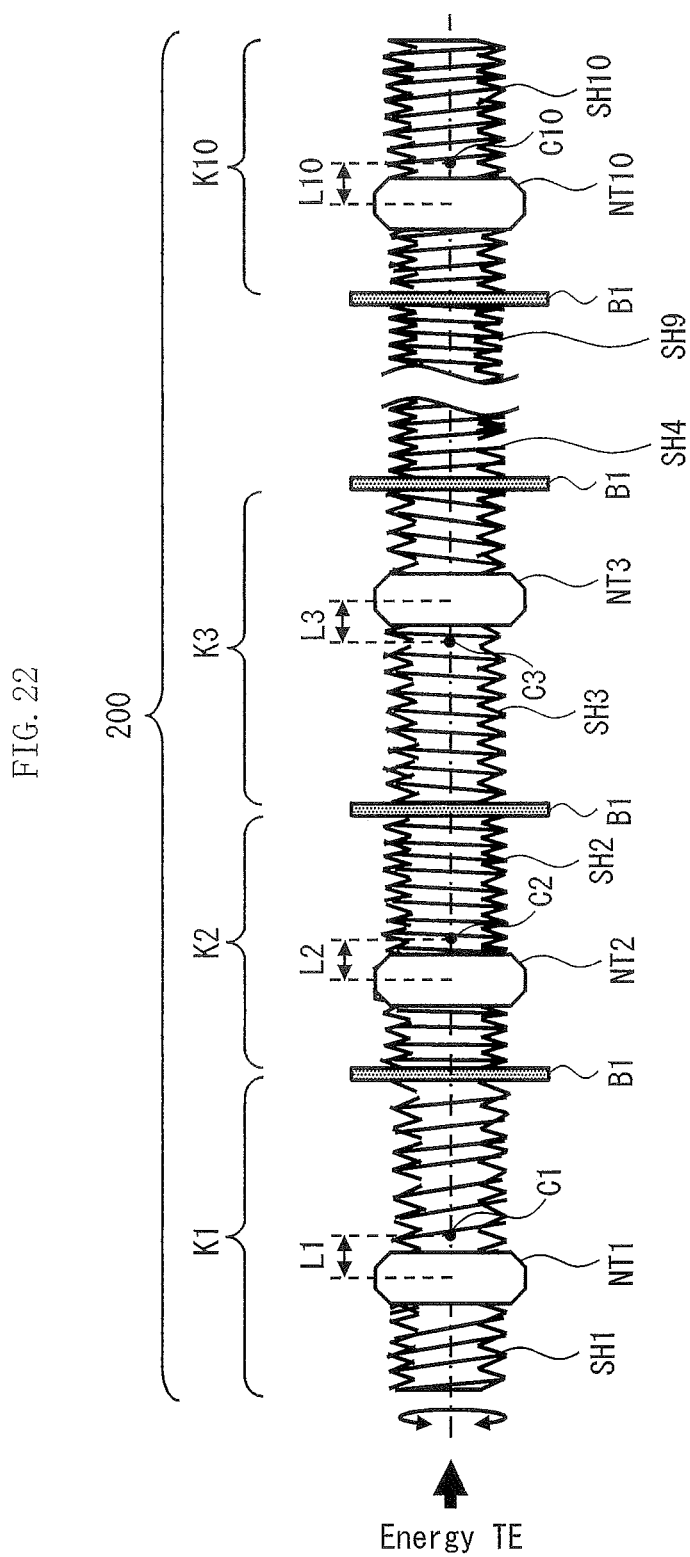
FIG. 22 is a diagram illustrating an example of a calculation model of a circulation system which is used for simulation of homeostasis in a subject by an examination unit illustrated in FIG. 20.

FIG. 22 illustrates an example of a calculation model of the circulation system 200 which is used for simulation of homeostasis in a subject PA by the examination unit 40 illustrated in FIG. 20. For example, the calculation model of the circulation system 200 illustrated in FIG. 22 is constructed on a virtual space such as a computer device by representing the circulation systems K1 to K10 included in the circulation system 200 illustrated in FIG. 21 by shafts SH (SH1 to SH10). The length, pitch width, and orientation of a screw thread of each of the shafts SH1 to SH10, and the like are determined based on characteristics of the living body of a subject PA. In addition, the shafts SH1 to SH10 are connected to each other by a bonding portion B1 such that the centers of axes of the respective shafts are consistent with each other, thereby forming the circulation system 200. In addition, nuts NT1 to NT10 are disposed at the respective shafts SH1 to SH10 of the circulation systems K1 to K10. The examination unit 40 rotates, for example, the shaft SH to simulate homeostasis in the circulation system 200, and detects the state of homeostasis in each of the circulation systems K1 to K10 from changes in the positions of the nuts NT1 to NT10.

Meanwhile, the length, pitch width, orientation of a screw thread, and the like of the shaft SH1 of the circulation system K1 of the vocal cords are determined based on frequency characteristics such as a frequency distribution, an intonation, and a pitch frequency that are indicated by a sound signal of utterance of a subject PA. In addition, the length, pitch width, orientation of a screw thread, and the like of the shaft SH2 of the circulation system K2 of the heart are determined based on characteristics such as a time interval of a heartbeat of a subject PA and a frequency distribution of a heartbeat fluctuation. The length, pitch width, orientation of a screw thread, and the like of the shaft SH3 of the circulation system K3 of the digestive system are determined based on characteristics such as the length of the small intestine, large intestine, or the like of a subject PA or a moving speed of a contraction wave associated with peristalsis. The length, pitch width, orientation of a screw thread, and the like of the circulation system K4 of the immune system are determined based on characteristics such as the number of leukocytes including neutrophils, eosinophils, basophils, lymphocytes, monocytes, and the like in blood of a subject PA. The length, pitch width, orientation of a screw thread, and the like of the circulation system K5 of hormone are determined based on characteristics such as the amount of hormone synthesized or secreted by each organ of a subject PA and a speed at which hormone circulates through the body by body fluids such as blood.

In addition, the length, pitch width, orientation of a screw thread, and the like of the circulation system K6 of biomolecules are determined based on, for example, the intake of nucleic acids, proteins, and polysaccharides included in food or the like eaten by a subject PA, amino acids and various types of sugar which are the components thereof, lipid, vitamin, and the like. The length, pitch width, orientation of a screw thread, and the like of the circulation system K7 of the gene are determined based on characteristics such as the frequency of fission of a gene of a subject PA and the length of the gene. In addition, the length, pitch width, orientation of a screw thread, and the like of the circulation system K8 of the cell are determined based on characteristics such as the amount of carbohydrates, lipids, proteins (amino acids), nucleic acids, or the like included in the cell of a subject PA and the lifespan of the cell. The length, pitch width, orientation of a screw thread, and the like of the circulation system K9 of the brain are determined based on characteristics such as a change over time in the activity of the brain including amygdala, a frequency distribution, and the like in the brain of a subject PA. The length, pitch width, orientation of a screw thread, and the like of the circulation system K10 of the neurotransmitter are determined based on, for example, the secreted amount of amino acids, peptides, or monoamines that mediate the transmission of information at synapses of a subject PA, a characteristic reaction rate, and the like.

Information indicating the length, pitch width, orientation of a screw thread, and the like of each of the shafts SH1 to SH10 which are set is stored in advance in the storage unit 50 for each subject PA. In addition, for example, the examination unit 40 may receive information indicating the length, pitch width, orientation of a screw thread, and the like of each of the shafts SH1 to SH10 of a subject PA through an input device, such as a keyboard or a touch panel, which is included in the estimation device 100a.

The examination unit 40 calculates energy acting on an emotion and organ activity of a subject PA from the shift amount of homeostasis in each of the circulation systems K1 to K10 which is calculated by the calculation unit 20a. For example, as illustrated in FIG. 12(b), similarly to the calculation unit 20 illustrated in FIG. 2, when a balanced position P1 of an emotion of a subject PA which is calculated by the calculation unit 20a is different from the center of the coordinate system, it is shown that the emotion of the subject PA, that is, the homeostasis of the circulation system K1 is displaced from a predetermined state and is shifted. For example, the shift of homeostasis appears in the subject PA in the form of stress, and affects not only the circulation system K1 of the subject PA but also the other circulation systems K2 to K10 such as the heart or the digestive system. Consequently, for example, the examination unit 40 calculates energy, such as stress, which acts on an emotion and organ activity of the subject PA from the shift amount of homeostasis in each of the circulation systems K1 to K10 which is calculated by the calculation unit 20a. For example, the examination unit 40 calculates an energy E(K1) from shift amounts $\alpha$, $\beta$, and $\gamma$ of homeostasis of emotions which are calculated by the calculation unit 20a in the circulation system K1 of the vocal cords, using Expression (1).

$$E(K1) = \mathrm{sqrt}(\alpha \times \alpha + \beta \times \beta + \gamma \times \gamma) \tag{1}$$

Meanwhile, as indicated by Expression (1), the examination unit 40 calculates the energy E(K1) generated in the circulation system K1 of the vocal cords from the shift amounts $\alpha$, $\beta$, and $\gamma$ of homeostasis of emotions, but may calculate the energy E(K1) using functions F ($\alpha$, $\beta$, $\gamma$) using the shift amounts $\alpha$, $\beta$, and $\gamma$ of homeostasis of emotions as variables.

The examination unit 40 calculates calories consumed due to stress, exercise, or the like, a food intake, and the like as energies E(K2) to E(K10), from the shift amounts of homeostasis in the respective circulation systems K which are calculated by the calculation unit 20a, with respect to the circulation systems K2 to K10. The examination unit 40 adds up the energies calculated in the respective circulation systems K1 to K10 using Expression (2).

$$TE = E(K1) + E(K2) + E(K3) + E(K4) + E(K5) + E(K6) + E(K7) + E(K8) + E(K9) + E(K10) \tag{2}$$

Here, E(K2), E(K3), E(K4), E(K5), E(K6), E(K7), E(K8), E(K9), and E(K10) indicate energies generated in the respective circulation systems K2 to K10. TE indicates a total energy. Meanwhile, the examination unit 40 obtains the energy TE by adding up the energies E(K1) to E(K10) generated in the respective circulation systems K1 to K10, but may obtain the energy TE by performing weighted addition of the energies E(K1) to E(K10). Alternatively, the examination unit 40 may obtain the energy TE by multiplying the energies E(K1) to E(K10) by each other.

The examination unit 40 inputs the calculated energy TE to the circulation system 200 to thereby rotate the shafts SH at a rotation speed depending on the magnitude of the energy TE. In addition, the examination unit 40 rotates the shafts SH clockwise, for example, when the energy TE has a positive value, and rotates the shafts SH counterclockwise when the energy TE has a negative value. Meanwhile, the energy TE which is input is controlled by the examination unit 40 so that displacement amounts L1 to L10 by which the respective nuts NT1 to NT10 are displaced in accordance with the rotation of the shafts SH fall inside ranges of lengths of the respective shafts SH1 to SH10.

In addition, the reason why the energy TE is set to have a positive or negative value is because, for example, energy for rotating the shafts SH clockwise or counterclockwise is generated in the circulation systems K1 to K10 in accordance with the orientation of a screw thread of each of the shafts SH1 to SH10. That is, for example, positive energy is generated in the circulation system K in which the shaft SH is rotated clockwise by the orientation of the screw thread, and negative energy is generated in the circulation system K in which the shaft SH is rotated counterclockwise. Meanwhile, for example, the examination unit 40 may rotates all of the shafts SH1 to SH10 clockwise when the energy TE has a negative value, and may rotate all of the shafts SH1 to SH10 counterclockwise when the energy TE has a positive value.

The examination unit 40 displaces the positions of the nuts NT1 to NT10 by rotating the shafts SH1 to SH10 by the energy TE. The examination unit 40 detects the displacement amounts L1 to L10 of the respective nuts NT1 to NT10 from the centers C1 to C10 of the respective shafts SH1 to SH10 as changes (or shift amounts of homeostasis) in the homeostasis of the respective circulation systems K1 to K10. For example, the examination unit 40 store the detected displacement amounts L1 to L10 in the storage unit 50 as data 60. In addition, the examination unit 40 detects speeds at which the nuts NT1 to NT10 move in axial directions of the respective shafts SH1 to SH10, from the displacement amounts L1 to L10. The examination unit 40 inputs the speeds detected in the circulation systems K1 to K10 to the circulation system 200 as energies E(K1) to E(K10) that are newly generated.

Meanwhile, when the calculation unit 20a calculates shift amounts of homeostasis in some circulation systems K among the circulation systems K1 to K10, the examination unit 40 may obtain an energy TE from the shift amounts of homeostasis in some circulation systems K which are calculated by the calculation unit 20a, and may simulate the homeostasis of the circulation system 200 based on the obtained energy TE. In addition, the examination unit 40 may detect all of the displacement amounts L1 to L10 in the circulation systems K1 to K10 from the simulation. The examination unit 40 detects displacement amounts L of all of the circulation systems K from the simulation, and thus the estimation device 100a can estimate the pathology of a subject PA with a higher level of accuracy than when the shift amounts of homeostasis in the circulation systems K which are calculated by the calculation unit 20a are used.

In addition, the examination unit 40 sets distances of the shafts SH1 to SH10 from the respective centers C1 to C10 as the displacement amounts L1 to L10 in the respective circulation systems K1 to K10, but the invention is not limited thereto. For example, the displacement amounts L1 to L10 may be distances between the nuts NT1 to NT10 or may be distances from a bonding portion B1.

FIG. 23 illustrates an example of data 60 of displacement amounts L1 to L10 in the respective circulation systems K1 to K10 of a subject PA. The data 60 includes storage regions of dates and the circulation systems K1 to K10.

The storage region of the date stores the date and time when, for example, the examination unit 40 performs simulation of a change in the homeostasis of the circulation system 200 and detects the displacement amounts L1 to L10 in the respective circulation systems K1 to K10 (for example, 2013/10/29 09:10:00, and the like). A time interval at which the examination unit 40 detects the displacement amounts L1 to L10 is one minute, one hour, one day, one week, one month, or the like, and is set to, for example, one hour in the case of the data 60 illustrated in FIG. 23.

The storage regions of the respective circulation systems K1 to K10 store, for example, the displacement amounts L1 to L10 of the respective nuts NT1 to NT10 which are detected by the examination unit 40. Meanwhile, a unit of each of the displacement amounts L1 to L10 is a centimeter, a millimeter, or the like.

The estimation unit 30a reads out the dates of the data 60 and the displacement amounts L1 to L10 in the respective circulation systems K1 to K10 from the storage unit 50. The estimation unit 30a estimates the pathology of a subject PA from patterns of changes over time in the read-out displacement amounts L1 to L10. For example, the storage unit 50 stores, in advance, data of a pattern of a typical change over time in each of the displacement amounts L1 to L10 indicated by the respective circulation systems K1 to K10 when the subject PA is healthy. In addition, the estimation unit 30a compares changes over time in the displacement amounts L1 to L10 detected by the examination unit 40 with typical changes over time in the displacement amounts L1 to L10 when the subject PA is healthy, and estimates the pathology of the subject PA from a comparison result. For example, the estimation unit 30a obtains a difference between the changes over time in the displacement amounts L1 to L10 detected by the examination unit 40 and the typical changes over time in the displacement amounts L1 to L10 when the subject PA is healthy, and compares the obtained difference with a predetermined threshold value indicating each pathology. That is, for example, in the case of the circulation system K2 of the heart, the estimation unit 30a obtains a difference between a change over time in the displacement amount L2 detected by the examination unit 40 and a typical change over time in the displacement amount L2 when the subject PA is healthy. The estimation unit 30a compares a predetermined threshold value, indicating heart disease such as myocardial infarction or angina pectoris, which is set in advance with the obtained difference, and estimates whether or not the subject PA suffers from heart disease such as myocardial infarction or angina pectoris.

Figure 24:
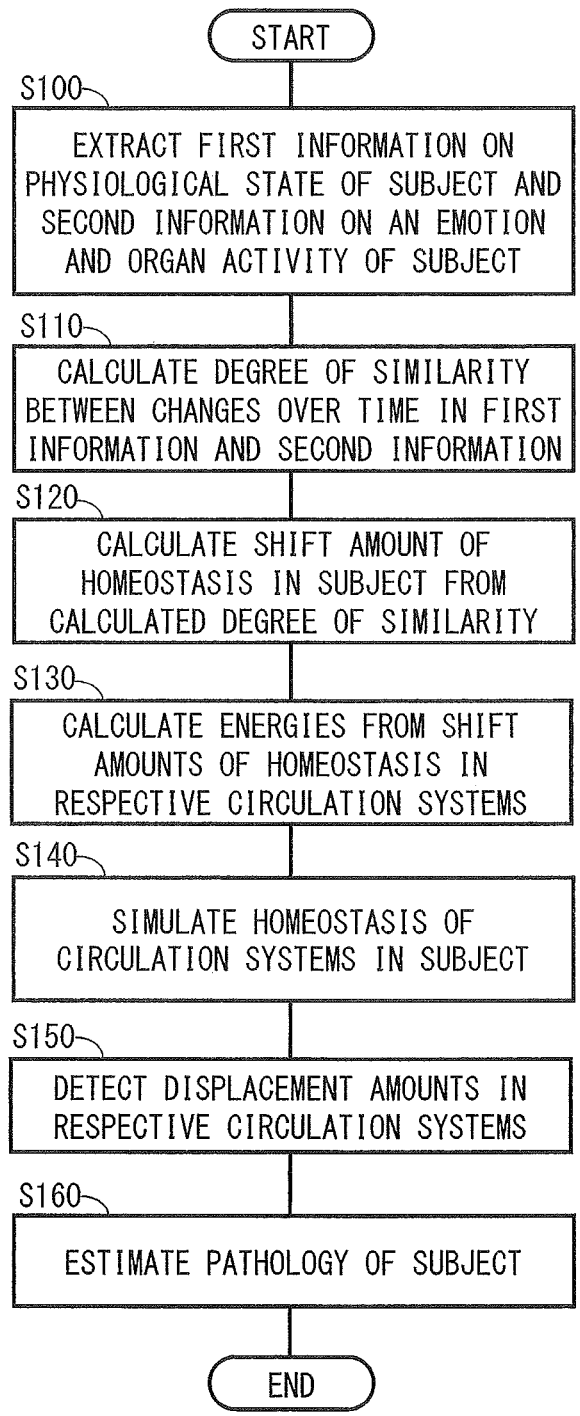
FIG. 24 is a diagram illustrating an example of an estimation process which is performed by the estimation device illustrated in FIG. 20.

FIG. 24 illustrates an example of an estimation process performed by the estimation device 100a illustrated in FIG. 20. Steps S100 to S160 are realized by a CPU, mounted on the estimation device 100a, executing an estimation program. That is, FIG. 24 illustrates an estimation program and an estimation method according to another embodiment. In this case, the extraction unit 10a, the calculation unit 20a, the estimation unit 30a, and the examination unit 40 illustrated in FIG. 20 are realized by the execution of the estimation program. Meanwhile, the process illustrated in FIG. 24 may be realized by hardware mounted on the estimation device 100a. In this case, the extraction unit 10a, the calculation unit 20a, the estimation unit 30a, and the examination unit 40 illustrated in FIG. 20 are realized by circuits disposed within the estimation device 100a.

In step S100, as described in FIG. 20, the extraction unit 10a extracts first information indicating a physiological state of a subject PA and second information indicating an emotion and the state of organ activity, based on information indicating the physiology of the subject PA which is measured by the measurement device 1a.

In step S110, as described in FIG. 21, the calculation unit 20a performs a mutual correlation process on changes over time in the first information and the second information which are extracted, to thereby calculate a mutual correlation coefficient indicating the degree of similarity.

In step S120, as described in FIGS. 12 and 21, the calculation unit 20a obtains a shift amount of homeostasis of the subject PA in each of the circulation systems K1 to K10 based on the obtained mutual correlation coefficient.

In step S130, as described in FIG. 22, the examination unit 40 calculates energies E(K1) to E(K10) from shift amounts of homeostasis in the respective circulation systems K1 to K10 which are calculated by the calculation unit 20a. The examination unit 40 obtains an energy TE by adding up the calculated energies E(K1) to E(K10), using Expression (2).

In step S140, as described in FIG. 22, the examination unit 40 inputs the energy TE obtained by the adding-up performed in step S130 to the circulation system 200 to thereby simulate the homeostasis of the circulation system 200 in the subject PA.

In step S150, as described in FIG. 22, the examination unit 40 detects the displacement amounts L1 to L10 in the respective circulation systems K1 to K10 from the simulation of homeostasis which is performed in step S140. The examination unit 40 stores the detected displacement amounts L1 to L10 in the respective circulation systems K1 to K10 in the storage unit 50 as data 60.

In step S160, as described in FIG. 23, the estimation unit 30a estimates the pathology of a subject PA from patterns of changes over time in the displacement amounts L1 to L10 in the respective circulation systems K1 to K10. For example, the estimation unit 30a compares the patterns of changes over time in the displacement amounts L1 to L10 detected by the examination unit 40 with typical patterns of changes over time in the displacement amounts L1 to L10 when the subject PA is healthy, and estimates the pathology of the subject PA from a comparison result.

In addition, the estimation process performed by the estimation device 100a is terminated. A flow illustrated in FIG. 24 may be repeatedly performed whenever an instruction is given from a doctor or a subject PA, or may be performed at a predetermined frequency. In addition, the estimation device 100a outputs an estimation result to the output device 2. The output device 2 displays a result of the estimated pathology and a shift amount of homeostasis. In addition, the output device 2 may represent the magnitude of a shift amount of homeostasis, that is, the degree of a symptom of the estimated pathology or a degree indicating the health of the subject PA by a color or a facial expression of a person, an animal, or the like of an animation, and may display the magnitude on a display. In addition, the output device 2 may display an advice such as a method for treatment of the estimated pathology in accordance with the magnitude of a shift amount of homeostasis.

As described above, in the embodiment illustrated in FIGS. 20 to 24, a shift amount of homeostasis in a subject PA is calculated using first information indicating a physiological state of the subject PA and second information indicating an emotion and organ activity of the subject PA. Thereby, the estimation device 100a can easily estimate the pathology of the subject PA without having expert knowledge on medicine with reference to an index such as a shift amount of the homeostasis. In addition, the estimation device 100a performs simulation of homeostasis of the subject PA using a shift amount of homeostasis in each circulation system K as an input energy. The estimation device 100a can compare a change over time in the homeostasis detected from the simulation performed with a change over time in the homeostasis which is shown when the subject PA is healthy, to thereby estimate the pathology of the subject PA with a higher level of accuracy than in the related art.

Figure 25:
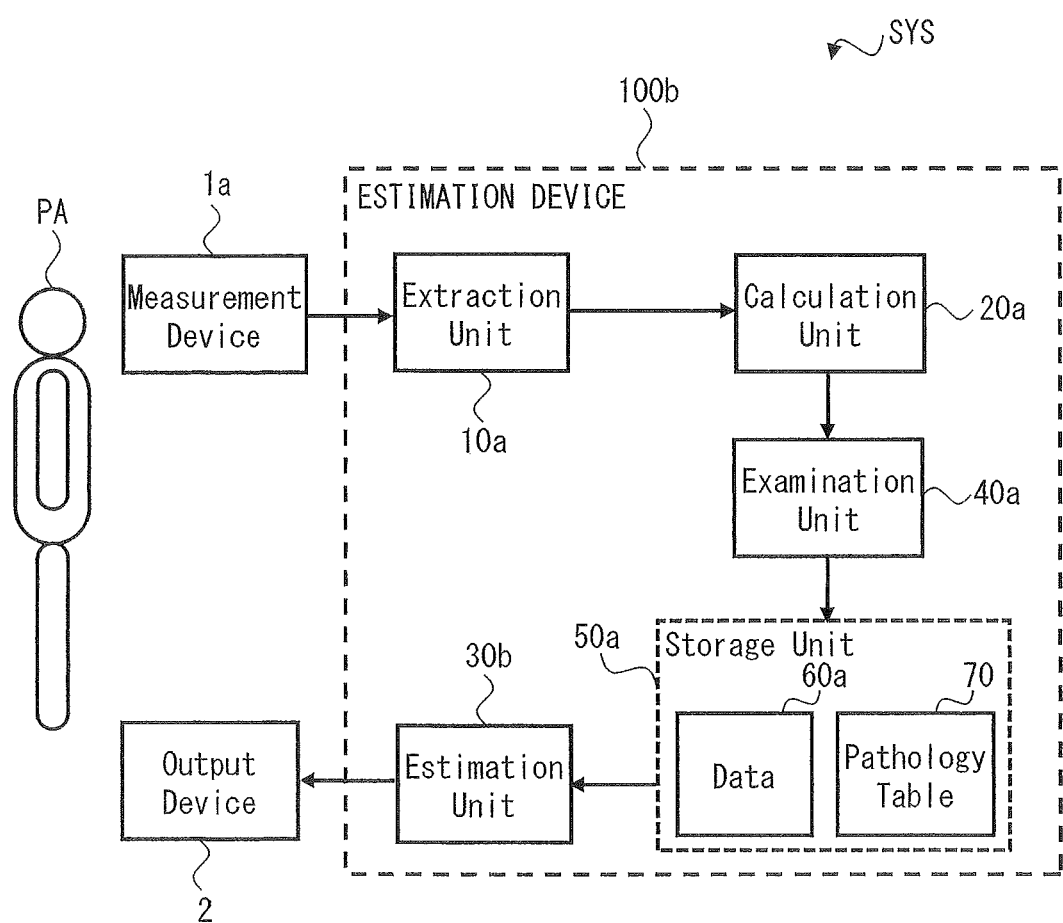
FIG. 25 is a diagram illustrating an estimation device according to further still another embodiment.

FIG. 25 illustrates an estimation device according to another embodiment. Components having functions that are the same as or similar to those of the components described in FIG. 20 will be denoted by the same or similar reference numerals and signs, and a detailed description thereof will be omitted. For example, an estimation device 100b, a measurement device 1a, and an output device 2 operate as an estimation system SYS.

The estimation device 100b illustrated in FIG. 25 is a computer device or the like which includes an arithmetic processor such as a CPU and a storage device such as a hard disk device. The estimation device 100b is connected to a measurement device 1a and the output device 2 through an interface unit included in the estimation device 100b in a wired or wireless manner. Thereby, the estimation device 100b, the measurement device 1a, and the output device 2 operate as an estimation system SYS.

In addition, the estimation device 100b includes an extraction unit 10a, a calculation unit 20a, an estimation unit 30b, an examination unit 40a, and a storage unit 50a. Functions of the extraction unit 10a, the calculation unit 20a, the estimation unit 30b, and the examination unit 40a may be realized by a program executed by a CPU or may be realized by hardware.

The storage unit 50a is a hard disk device, a memory, or the like. The storage unit 50a stores a program executed by a CPU. In addition, the storage unit 50a stores data 60a indicating a result of simulation performed by the examination unit 40a, and a pathology table 70 for making the estimation unit 30b determine the pathology of a subject PA using the data 60a. The data 60a and the pathology table 70 will be described with reference to FIGS. 27 and 28.

Meanwhile, a program for executing an estimation process can be recorded in a removable disc such as a CD or a DVD and can be distributed. In addition, the estimation device 100b may download the program for executing an estimation process from a network through a network interface included in the estimation device 100b, and may store the downloaded program in the storage unit 50a.

The examination unit 40a calculates energy acting on an emotion and organ activity of a subject PA from a shift amount of homeostasis which is calculated by the calculation unit 20a. The examination unit 40a inputs the calculated energy to a calculation model indicating the living body of the subject PA to simulate homeostasis in the subject PA. The calculation model and the operation of the examination unit 40a will be described with reference to FIG. 26.

The estimation unit 30b estimates the pathology of a subject PA from a pattern of a change in the homeostasis simulated by the examination unit 40a. The operation of the estimation unit 30b will be described with reference to FIGS. 27 and 28.

Figure 26:
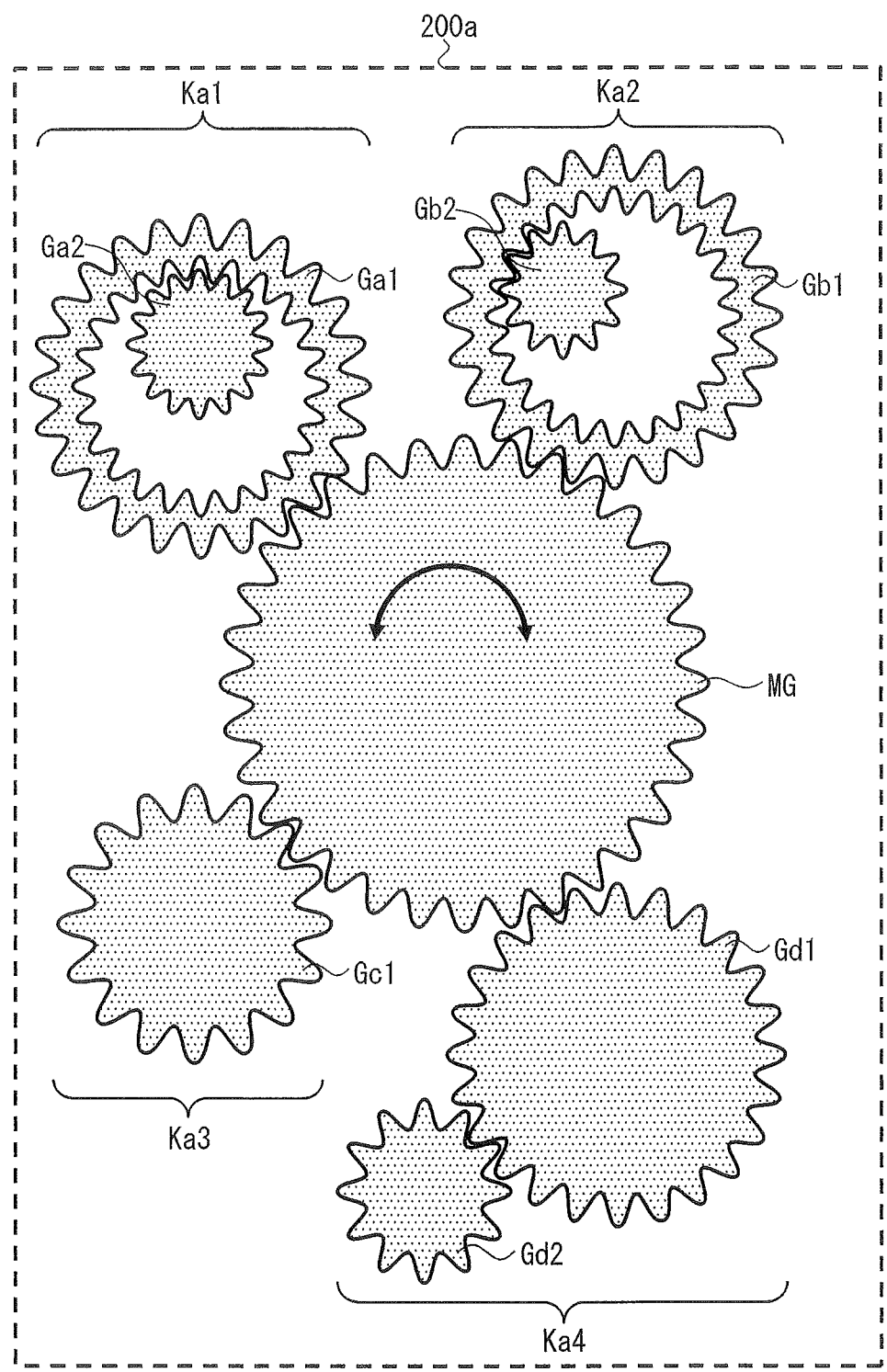
FIG. 26 is a diagram illustrating an example of a calculation model of a circulation system which is used for simulation of homeostasis in a subject by the examination unit illustrated in FIG. 25.

FIG. 26 illustrates an example of a calculation model of a circulation system 200a which is used for simulation of homeostasis in a subject PA by the examination unit 40a illustrated in FIG. 25. The calculation model of the circulation system 200a illustrated in FIG. 26 includes, for example, four circulation systems Ka (Ka1 to Ka4) included in the circulation system 200a. The circulation system 200a and the circulation systems Ka1 to Ka4 included in the circulation system 200a are represented by a gear MG and gears Ga1-Ga2, Gb1-Gb2, Gc1, and Gd1-Gd2, and are constructed on a virtual space such as a computer device. The gear MG is rotated based on energies E(Ka1) to E(Ka4) calculated from shift amounts of homeostasis in the respective circulation systems Ka1 to Ka4 which are obtained by the calculation unit 20a. The gears Ga1-Ga2, Gb1-Gb2, Gc1, and Gd1-Gd2 of the respective circulation systems Ka1 to Ka4 are rotated in association with the rotation of the gear MG. As illustrated in FIG. 26, each of the circulation systems Ka1, Ka2, and Ka4 includes two gears Ga1-Ga2, Gb1-Gb2, Gd1-Gd2, and the circulation system Ka3 includes one gear Gc1. Meanwhile, the diameter and number of teeth of the gear MG, and the number, diameter, number of teeth, and the like of gears included in each of the circulation systems Ka1 to Ka4 are determined based on characteristics of the living body of the subject PA. The examination unit 40a rotates, for example, the gear MG to thereby simulate the homeostasis of the circulation system 200a, and detects the state of homeostasis in each of the circulation systems Ka1 to Ka4 from the number of rotations of the gears Ga2, Gb2, Gc1, and Gd2.

Meanwhile, when the circulation system Ka is the vocal cords, the number, diameters, number of teeth, and the like of gears included in the circulation system Ka are determined based on, for example, frequency characteristics such as a frequency distribution, an intonation, and a pitch frequency in a sound signal of utterance of a subject PA. In addition, when the circulation system Ka is the heart, the number, diameters, number of teeth, and the like of gears included in the circulation system Ka are determined based on characteristics such as a time interval of a heartbeat and a frequency distribution of a heartbeat fluctuation. When the circulation system Ka is the digestive system, the number, diameters, number of teeth, and the like of gears included in the circulation system Ka are determined based on characteristics such as the length of the small intestine, large intestine, or the like or a moving speed of a contraction wave associated with peristalsis. When the circulation system Ka is the immune system, the number, diameters, number of teeth, and the like of gears included in the circulation system Ka are determined based on characteristics such as the number of leukocytes including neutrophils, eosinophils, basophils, lymphocytes, monocytes, and the like in blood of a subject PA.

In addition, when the circulation system Ka is hormone, the number, diameters, number of teeth, and the like of gears included in the circulation system Ka are determined based on characteristics such as the amount of hormone synthesized or secreted by each organ of a subject PA and a speed at which hormone circulates through the body by body fluids such as blood. When the circulation system Ka is a biomolecule, the number, diameters, number of teeth, and the like of gears included in the circulation system Ka are determined based on, for example, the intake of nucleic acids, proteins, and polysaccharides included in food or the like eaten by a subject PA, amino acids and various types of sugar which are the components thereof, lipid, vitamin, and the like. When the circulation system Ka is a gene, the number, diameters, number of teeth, and the like of gears included in the circulation system Ka are determined based on characteristics such as the frequency of fission of a gene of a subject PA and the length of the gene. In addition, when the circulation system Ka is a cell, the number, diameters, number of teeth, and the like of gears included in the circulation system Ka are determined based on characteristics such as the amount of carbohydrates, lipids, proteins (amino acids), nucleic acids, or the like included in the cell and the lifespan of the cell. When the circulation system Ka is the brain, the number, diameters, number of teeth, and the like of gears included in the circulation system Ka are determined based on characteristics such as a change over time in the activity of the brain including amygdala, a frequency distribution, and the like in the brain of a subject PA. When the circulation system Ka is the neurotransmitter, the number, diameters, number of teeth, and the like of gears included in the circulation system Ka are determined based on, for example, the secreted amount of amino acids, peptides, or monoamines that mediate the transmission of information at synapses, a characteristic reaction rate, and the like.

Information indicating the diameter and number of teeth of the gear MG and the number, diameter, number of teeth, and the like of each of the gears Ga1-Ga2, Gb1-Gb2, Gc1, and Gd1-Gd2 which are set is stored in advance in the storage unit 50 of the estimation device 100b for each subject PA. In addition, the examination unit 40 may receive the information indicating the diameter and number of teeth of the gear MG and the number, diameter, number of teeth, and the like of each of the gears Ga1-Ga2, Gb1-Gb2, Gc1, and Gd1-Gd2 through an input device such as a keyboard or the like included in the estimation device 100b.

Meanwhile, the circulation system 200a includes four circulation systems Ka1 to Ka4, but is not limited thereto. The circulation system may include any number of plurality of circulation systems other than four. In addition, each circulation system Ka may further include a plurality of circulation systems. For example, when the circulation system Ka is the vocal cords, the circulation system may include a plurality of gears that represent a plurality of circulation systems indicating emotions such as anger, normal, sorrow, and pleasure of a subject PA. In addition, when the circulation system Ka is the heart, the circulation system may include a plurality of gears that represent a plurality of circulation systems indicating, for example, a heart rate, a heartbeat fluctuation, and the like of a subject PA.

Similarly to the examination unit 40 illustrated in FIG. 20, the examination unit 40a calculates an energy TE from shift amounts of homeostasis in the respective circulation systems Ka1 to Ka4 which are calculated by the calculation unit 20a, using Expression (1) and Expression (2). The examination unit 40a inputs the calculated energy TE to the circulation system 200a to thereby rotate the gear MG at a rotation speed depending on the magnitude of the energy TE. For example, the examination unit 40a rotates the gear MG clockwise when the energy TE has a positive value, and rotates the gear MG counterclockwise when the energy TE has a negative value. Meanwhile, the examination unit 40a may rotate the gear MG counterclockwise, for example, when the energy TE has a positive value, and may rotate the gear MG clockwise when the energy TE has a negative value.

The examination unit 40a simulates a homeostasis in the circulation system 200a by rotating the gear MG and detects, for example, the state of homeostasis in each of the circulation systems Ka1 to Ka4 as the number of rotations of the gear. The examination unit 40a stores detected numbers of rotations R1 to R4 in the storage unit 50a. In addition, the examination unit 40a inputs the numbers of rotations R1 to R4 detected in the respective circulation systems Ka1 to Ka4 to the circulation system 200a as energies E(Ka1) to E(Ka4) that are newly generated.

Meanwhile, when the calculation unit 20a calculates shift amounts of homeostasis in some circulation systems Ka among the circulation systems Ka1 to Ka4, the examination unit 40a may obtain an energy TE from the shift amounts of homeostasis in some circulation systems Ka which are calculated by the calculation unit 20a, and may simulate the homeostasis of the circulation system 200a based on the obtained energy TE. In addition, the examination unit 40a may detect all of the numbers of rotations R1 to R4 in the circulation systems Ka1 to Ka4 from the simulation. The examination unit 40a detects the numbers of rotations R of all of the circulation systems Ka from the simulation, and thus the estimation device 100b can estimate the pathology of a subject PA with a higher level of accuracy than when the shift amounts of homeostasis in the circulation systems Ka which are calculated by the calculation unit 20a are used.

FIG. 27 illustrates an example of data 60a of the numbers of rotations R1 to R4 of the respective circulation systems Ka1 to Ka4 of a subject PA. The data 60a includes storage regions of dates and the circulation systems Ka1 to Ka4.

The storage region of the date stores the date and time when, for example, the examination unit 40a performs simulation of a change in the homeostasis of the circulation system 200 and detects the numbers of rotations R1 to R4 in the respective circulation systems Ka1 to Ka4 (for example, 2013/10/29 09:10:00, and the like). A time interval at which the examination unit 40a detects the numbers of rotations R1 to R4 is one minute, one hour, one day, one week, one month, or the like, and is set to, for example, one minute in the case of the data 60a illustrated in FIG. 27.

The storage regions of the respective circulation systems Ka1 to Ka4 store, for example, the numbers of rotations R1 to R4 (for example, 20 rotations per minute, or the like) of the respective gears Ga2, Gb2, Gc1, and Gd2 which are detected by the examination unit 40a.

FIG. 28 illustrates an example of a pathology table 70. The pathology table 70 includes storage regions of pathologies and the circulation systems Ka1 to Ka4.

The storage regions of the pathologies store pathologies such as major depression, depression, normal (that is, a subject PA is healthy), manic depression, and a personality disorder. Meanwhile, the pathology table 70 illustrated in FIG. 28 includes the psychiatric disorder as a pathology, but may include a heart disease such as myocardial infarction or a brain disease such as cerebral infarction.

The storage regions of the circulation systems Ka1 to Ka4 store conditions in which each of the pathologies stored in the storage regions of pathologies is estimated by the estimation unit 30b. Meanwhile, a storage region in which "-" is stored indicates that a condition for estimating the corresponding pathology is not included. For example, when each of the circulation systems Ka1 to Ka4 indicates an emotion such as anger, normal, sorrow, or pleasure and the numbers of rotations R1 to R4 in all of the emotions of anger, normal, sorrow, and pleasure are set to 0 (non-rotation), the estimation unit 30b estimates that a subject PA is in a major depression state. That is, the major depression indicates a state of the deviation of homeostasis that all of the emotions such as anger, normal, sorrow, and pleasure do not appear in the subject PA. In addition, when each of the circulation systems Ka1 to Ka4 indicates an emotion such as anger, normal, sorrow, or pleasure and the number of rotations R3 of sorrow is smaller than a threshold value $\alpha$ regardless of the numbers of rotations of the emotions of anger, normal, and pleasure, the estimation unit 30b estimates that a subject PA is in a depression state. That is, the depression indicates a state of the deviation of homeostasis that the frequency of appearance of the emotion of sorrow in the subject PA is low. Meanwhile, the threshold value $\alpha$ is set in advance and is stored in the storage unit 50a. In addition, the threshold value $\alpha$ may set to a value different for each subject PA.

In addition, when each of the circulation systems Ka1 to Ka4 indicates an emotion such as anger, normal, sorrow, or pleasure and the number of rotations R3 of sorrow is the number of rotations between the threshold value $\alpha$ and a threshold value $\beta$ ($\beta>\alpha$), the estimation unit 30b estimates a subject PA to be in a normal state (that is, the subject PA is healthy). That is, the pathology of normal indicates a state where the emotion of sorrow properly appears in the subject PA together with other emotions and homeostasis does not deviate. Meanwhile, the threshold value $\beta$ is set in advance and is stored in the storage unit 50a. In addition, the threshold value $\beta$ may be set to a value different for each subject PA.

In addition, when each of the circulation systems Ka1 to Ka4 indicates an emotion such as anger, normal, sorrow, or pleasure and the number of rotations R3 of sorrow is larger than the threshold value $\beta$, the estimation unit 30b estimates that a subject PA is in a manic depression state. That is, the manic depression indicates a state where the emotion of sorrow frequently appears in the subject PA and homeostasis deviates. In addition, an estimation result of the estimation unit 30b is a personality disorder when the number of rotations R1 of anger and the number of rotations R4 of pleasure are equal to each other regardless of the numbers of rotations of the emotions of normal and sorrow. That is, the personality disorder indicates a state where the emotions of anger and pleasure that are contrary to each other simultaneously appear in the subject PA.

Meanwhile, each of the circulation systems Ka1 to Ka4 is set to be an emotion such as anger, normal, sorrow, or pleasure. However, when a pathology is panic disorder, it is preferable that circulation systems of emotions such as anger, normal, sorrow, and pleasure and a circulation system such as a heartbeat are used.

The estimation unit 30b reads out the data 60a and the pathology table 70 from the storage unit 50a. The estimation unit 30b calculates the frequency of appearance of the number of rotations satisfying conditions of each of the circulation systems Ka1 to Ka4, which are indicated by the respective pathologies stored in the pathology table 70, for a predetermined period of time such as one day or two weeks, using the read-out data 60a. That is, for example, when the circulation systems Ka1 to Ka4 are set to be emotions such as anger, normal, sorrow, and pleasure, the estimation unit 30b calculates the frequency of appearance at which the numbers of rotations R1 to R4 are set to 0 (non-rotation), for a predetermined period of time for each circulation system Ka. In addition, the estimation unit 30b calculates frequencies of appearance in respective cases where the number of rotations R3 in the circulation system Ka3 of sorrow is smaller than the threshold value $\alpha$, is between the threshold value $\alpha$ and the threshold value $\beta$, and is larger than the threshold value $\beta$ for a predetermined period of time. Further, the estimation unit 30b calculates the frequency of appearance at which the number of rotations R1 of the circulation system Ka1 of anger and the number of rotations R4 of the circulation system Ka4 of pleasure become equal to each other for a predetermined period of time. The frequency of appearance of the number of rotations of each circulation system Ka for a predetermined period of time is an example of a pattern of a change in a homeostasis.

For example, the estimation unit 30b extracts conditions indicating the frequency of appearance which has a value equal to or greater than a threshold value Th among the calculated frequencies of appearance. The estimation unit 30b estimates a pathology satisfying a combination of the extracted conditions as the pathology of a subject PA, using the extracted conditions and the pathology table 70. Meanwhile, the predetermined period of time is determined based on a standard of mental medical care such as ICD-10. In addition, the threshold value Th is set in advance and is stored in the storage unit 50a. In addition, the threshold value Th may be set to a value different for each subject PA and each pathology.

Meanwhile, the estimation unit 30b calculates the frequencies of appearance of the numbers of rotations R1 to R4 in the respective circulation systems Ka1 to Ka4, but may calculate an average value and deviation of the numbers of rotations R1 to R4 in the respective circulation systems Ka1 to Ka4 for a predetermined period of time. In addition, the estimation unit 30b may compare changes over time in the calculated average value and deviation of the numbers of rotations R1 to R4 in the respective circulation systems Ka1 to Ka4 with typical changes over time in an average value and deviation when a subject PA is healthy to thereby estimate the pathology of the subject PA from a comparison result.

Figure 29:
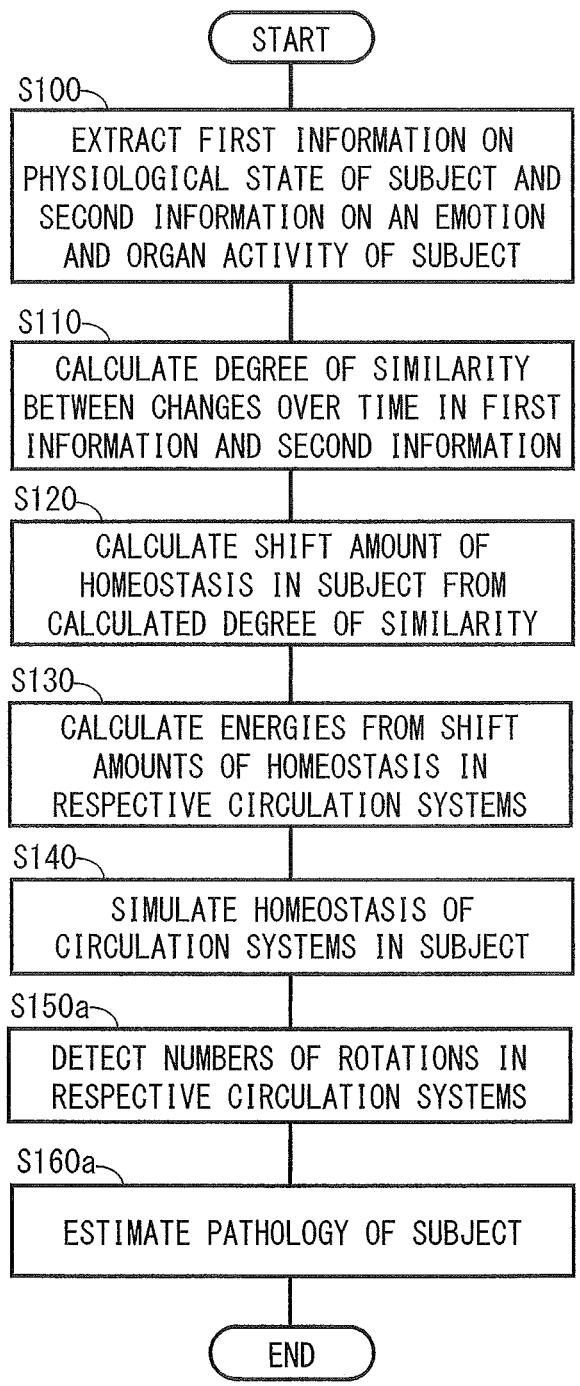
FIG. 29 is a diagram illustrating an example of an estimation process which is performed by the estimation device illustrated in FIG. 25.

FIG. 29 illustrates an example of an estimation process performed by the estimation device 100b illustrated in FIG. 25. Meanwhile, among processes of steps illustrated in FIG. 29, the same step number will be attached to steps indicating processes that are the same as or similar to those of the steps illustrated in FIG. 24, and a detailed description thereof will be omitted. Step S100 to step S140, step S150a, and step S160a are realized by a CPU, mounted on the estimation device 100b, executing an estimation program. That is, FIG. 29 illustrates an estimation program and an estimation method according to another embodiment. In this case, the extraction unit 10a, the calculation unit 20a, the estimation unit 30b, and the examination unit 40a illustrated in FIG. 25 are realized by executing an estimation program. Meanwhile, processes illustrated in FIG. 29 may be realized by hardware mounted on the estimation device 100b. In this case, the extraction unit 10a, the calculation unit 20a, the estimation unit 30b, and the examination unit 40a illustrated in FIG. 25 are realized by circuits disposed within the estimation device 100b.

The estimation device 100b performs processes of step S100 to step S140 illustrated in FIG. 29 and then performs a process of step S150a.

In step S150a, the examination unit 40a detects the numbers of rotations R1 to R4 in the respective circulation systems Ka1 to Ka4 from simulation of homeostasis which is performed in step S140, as described in FIG. 26. The examination unit 40a stores the detected numbers of rotations R1 to R4 in the respective circulation systems Ka1 to Ka4 in the storage unit 50a as data 60a.

In step S160a, the estimation unit 30b estimates the pathology of a subject PA based on the data 60a of the numbers of rotations R1 to R4 in the respective circulation systems Ka1 to Ka4 and the pathology table 70, as described in FIGS. 27 and 28.

In addition, the estimation process performed by the estimation device 100b is terminated. A flow illustrated in FIG. 29 may be repeatedly performed whenever an instruction is given from a doctor or a subject PA, or may be performed at a predetermined frequency. In addition, the estimation device 100b outputs an estimation result to the output device 2. The output device 2 displays a result of the estimated pathology and a shift amount of homeostasis. In addition, the output device 2 may represent the magnitude of a shift amount of homeostasis, that is, the degree of a symptom of the estimated pathology or a degree indicating the health of the subject PA by a color or a facial expression of a person, an animal, or the like of an animation, and may display the magnitude on a display. In addition, the output device 2 may display an advice such as a method for treatment of the estimated pathology in accordance with the magnitude of a shift amount of homeostasis.

As described above, in the embodiment illustrated in FIGS. 25 to 29, a shift amount of homeostasis in a subject PA is calculated using first information indicating a physiological state of the subject PA and second information indicating an emotion and organ activity of the subject PA. Thereby, the estimation device 100b can easily estimate the pathology of the subject PA without having expert knowledge on medicine with reference to an index such as a shift amount of the homeostasis. In addition, the estimation device 100b performs simulation of homeostasis in the subject PA using shift amounts of homeostasis in the respective circulation systems Ka as input energy. The estimation device 100b compares the frequency of appearance of the number of rotations in each circulation system Ka which indicates a change in the homeostasis detected from the performed simulation with the frequency of appearance of the number of rotations in each circulation system Ka which is indicated when a subject PA is healthy. In addition, the estimation device 100b can estimate the pathology of the subject PA with a higher level of accuracy than in the related art, using a comparison result and the pathology table 70.

Figure 30:
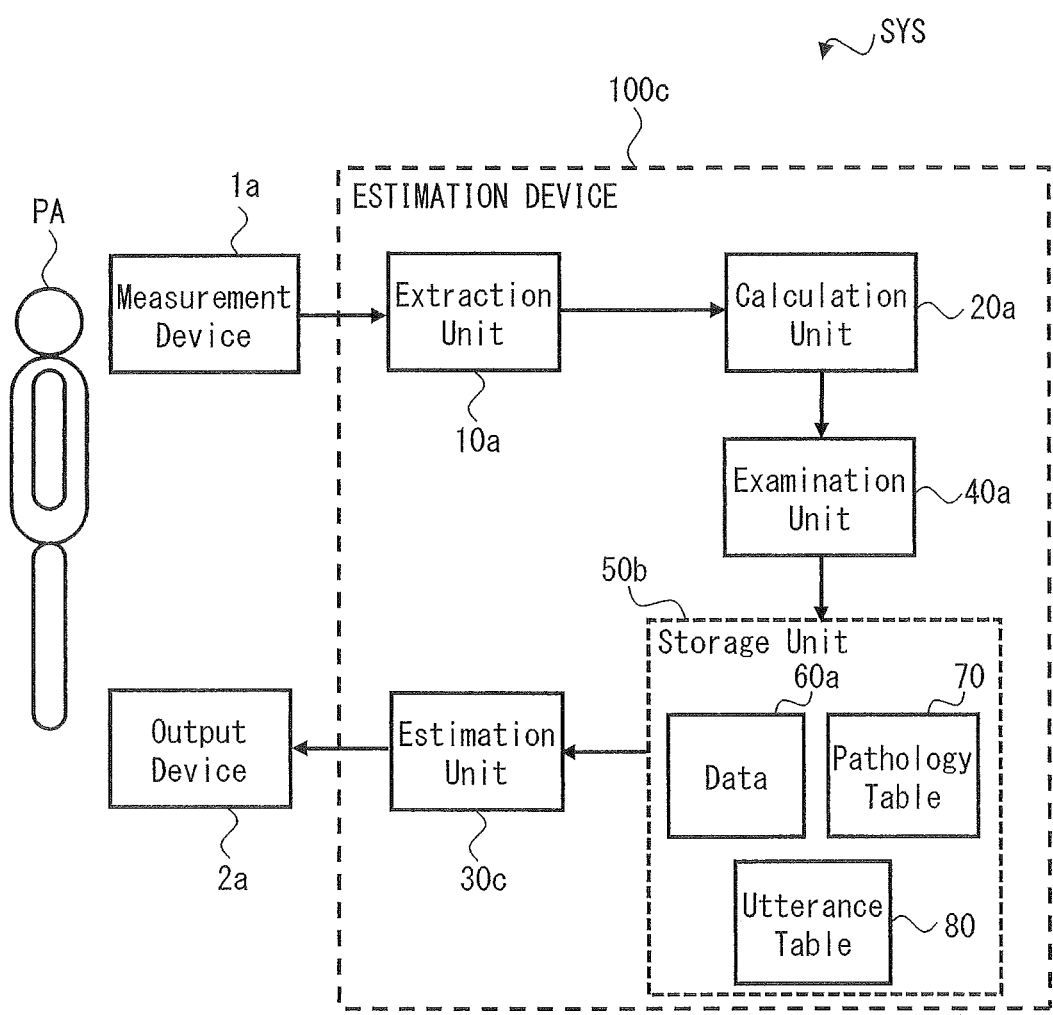
FIG. 30 is a diagram illustrating an estimation device according to further still another embodiment.

FIG. 30 illustrates an estimation device according to another embodiment. Components having functions that are the same as or similar to those of the components described in FIG. 25 will be denoted by the same or similar reference numerals and signs, and a detailed description thereof will be omitted. An estimation device 100c is a computer device or the like which includes an arithmetic processor such as a CPU and a storage device such as a hard disk device. The estimation device 100c is connected to a measurement device 1a and an output device 2a through an interface unit included in the estimation device 100c in a wired or wireless manner. Thereby, the estimation device 100c, the measurement device 1a, and the output device 2a operate as an estimation system SYS.

The output device 2a includes a display such as an organic EL or a liquid crystal, and a speaker that outputs a sound. The output device 2a receives an estimation result of the pathology of a subject PA which is obtained by the estimation device 100c, and displays the received estimation result on the display such as an organic EL. In addition, the output device 2a outputs an advice or the like according to the pathology estimated by the estimation device 100c as a sound. Meanwhile, the output device 2a may be disposed within the estimation device 100c.

In addition, the estimation device 100c includes an extraction unit 10a, a calculation unit 20a, an estimation unit 30c, an examination unit 40a, and a storage unit 50b. Functions of the extraction unit 10a, the calculation unit 20a, the estimation unit 30c, and the examination unit 40a may be realized by a program executed by a CPU or may be realized by hardware.

The storage unit 50b is a hard disk device, a memory, or the like. The storage unit 50b stores programs executed by a CPU, data 60a indicating results of simulation performed by the examination unit 40a, and a pathology table 70 for allowing the estimation unit 30c to estimate the pathology of a subject PA using the data 60a. In addition, the storage unit 50b stores an utterance table 80 including sound data such as an advice on a subject PA based on the pathology estimated by the estimation unit 30c. The utterance table 80 will be described with reference to FIG. 31.

Meanwhile, a program for executing an estimation process can be recorded in a removable disc such as a CD or a DVD and can be distributed. In addition, the estimation device 100c may download the program for executing an estimation process from a network through a network interface included in the estimation device 100c, and may store the downloaded program in the storage unit 50b.

The estimation unit 30c estimates the pathology of a subject PA from a pattern of a change in the homeostasis simulated by the examination unit 40a. In addition, the estimation unit 30c selects sound data such as an advice on a subject PA based on the estimated pathology of the subject PA and the utterance table 80. The operation of the estimation unit 30c will be described with reference to FIG. 31.

FIG. 31 illustrates an example of the utterance table 80. The utterance table 80 includes pathologies and storage regions of utterances.

The storage regions of the pathologies store pathologies such as major depression, depression, a personality disorder (male), and a personality disorder (female). Meanwhile, in the case of the personality disorder, treatment is different between a male and a female, and thus the utterance table 80 includes storage regions of personality disorders for a male and a female. In addition, the utterance table 80 includes the psychiatric disorder as a pathology, but may include storage regions of a heart disease such as myocardial infarction or other brain diseases such as cerebral infarction.

The storage regions of the utterances store sound data such as an advice on a subject PA based on a standard of mental medical care such as ICD-10, in accordance with each pathology stored in the storage regions of the pathologies. For example, when the estimation unit 30c estimates that a subject PA is in a major depression state, it is estimated that a symptom of depression in the subject PA is in its advanced stage. Consequently, in order for the estimation device 100c to function as a teacher or trainer of the subject PA, sound data such as "Go to the hospital quickly" for leading the subject PA is stored in the storage region of the utterance. In addition, when the estimation unit 30c estimates that a subject PA is in a depression state, it is estimated that the subject PA is in a depression state. Consequently, in order for the estimation device 100c to functions as a teacher or a trainer of a subject PA, sound data such as "Don't just stay at home. Let's go for a walk outside once in a while" for training the mind of the subject PA by getting close to the subject PA is stored in the storage region of the utterance. That is, when a subject PA is in a major depression state, a depression state, or the like, sound data for making the estimation device 100c function as a teacher or a trainer of a subject PA is stored in the storage region of the utterance, and thus it is possible to achieve an improvement in a depression state in the subject PA and the strengthening of personality of the subject PA.

In addition, when it is estimated that a subject PA is a male and has a personality disorder, there is a tendency for the subject PA to be in an unilaterally aggressive state. Consequently, in order for the estimation device 100c to function as a counselor of a subject PA, sound data such as "You must think about not only yourself but also the other person's feeling" for reasoning the subject PA into evoking sympathy with the other person is stored in the storage region of the utterance. On the other hand, when it is determined that a subject PA is a female and has a personality disorder, there is a strong possibility of the subject PA doing self-injuring behavior such as wrist cutting. Consequently, in order for the estimation device 100c to function as a counselor of a subject PA, sound data such as "You are always doing your best. So, stop doing such a thing" for leading the subject PA to have sympathy while encouraging the subject by getting close to the subject PA is stored in the storage region of the utterance. That is, when the subject PA has a personality disorder or the like, sound data for making the estimation device 100c function as a counselor of the subject PA is stored in the storage region of the utterance, and thus it is possible to evoke sympathy of the subject PA and to achieve an improvement in personality of the subject PA.

Meanwhile, the storage region of the utterance may store an address indicating the region of the storage unit 50b in which sound data is stored, instead of storing sound data.

In addition, with regard to sound data stored in the storage region of the utterance of the utterance table 80, a plurality of pieces of sound data having different utterance contents based on a standard of mental medical care such as ICD-10 may be stored with respect to one pathology. For example, the extraction unit 10a extracts breaks for each phoneme from a sound signal of a subject PA. That is, when a sound of "The weather is nice today" is input, the extraction unit 10a extracts breaks for each phoneme like "Th/e/w/e/a/th/e/r/i/s/n/i/c/e/t/o/d/a/y". Further, the extraction unit 10a extracts breaks for each word from a sound signal of a subject PA. For example, when a sound of "The weather is nice today" is input, the extraction unit 10a extracts breaks for each word like "The/weather/is/nice/today".

In addition, the estimation unit 30c performs recognition and syntax analysis for each word included in a sound of a subject PA which is extracted by the extraction unit 10a, based on information indicating a phoneme and breaks of a word in the sound of the subject PA. That is, the estimation unit 30c recognizes information indicating 5W1H of "who", "what", "when", "where", "why", and "how" from a sound of a subject PA, and ascertains contents of the sound of the subject PA to be a natural language. In addition, the estimation unit 30c determines in what condition or situation the subject PA lies, from the sound of the subject PA based on the ascertained contents of the sound. In addition, the estimation unit 30c selects one of a plurality of pieces of sound data such as an advice on a pathology estimated in accordance with the determined condition or situation. Thereby, the estimation device 100c can perform finer treatment on the subject PA than in the related art.

In addition, the estimation unit 30c can perform treatment on a subject PA having a communication disorder by ascertaining contents of a sound of the subject PA. For example, the estimation unit 30c estimates whether or not the subject PA has a communication disorder, from an emotion of the subject PA which is extracted by the extraction unit 10a when the subject PA utters a predetermined word. For example, when an emotion such as anger is never extracted or is extracted just a little in a subject PA by the extraction unit 10a when the subject PA utters a predetermined word indicating an emotion such as anger, the estimation unit 30c estimates that the subject PA cannot read the atmosphere at the scene and has a communication disorder. When the estimation unit 30c estimates that the subject has a communication disorder, sound data such as "Please read the atmosphere" for leading the subject PA to have a communication power is read out from the storage region of the utterance in order for the estimation device 100c to function as a teacher or the like. Thereby, the estimation device 100c can perform treatment on the communication disorder of the subject PA so that the subject PA can read the atmosphere and perform communication.

Figure 32:
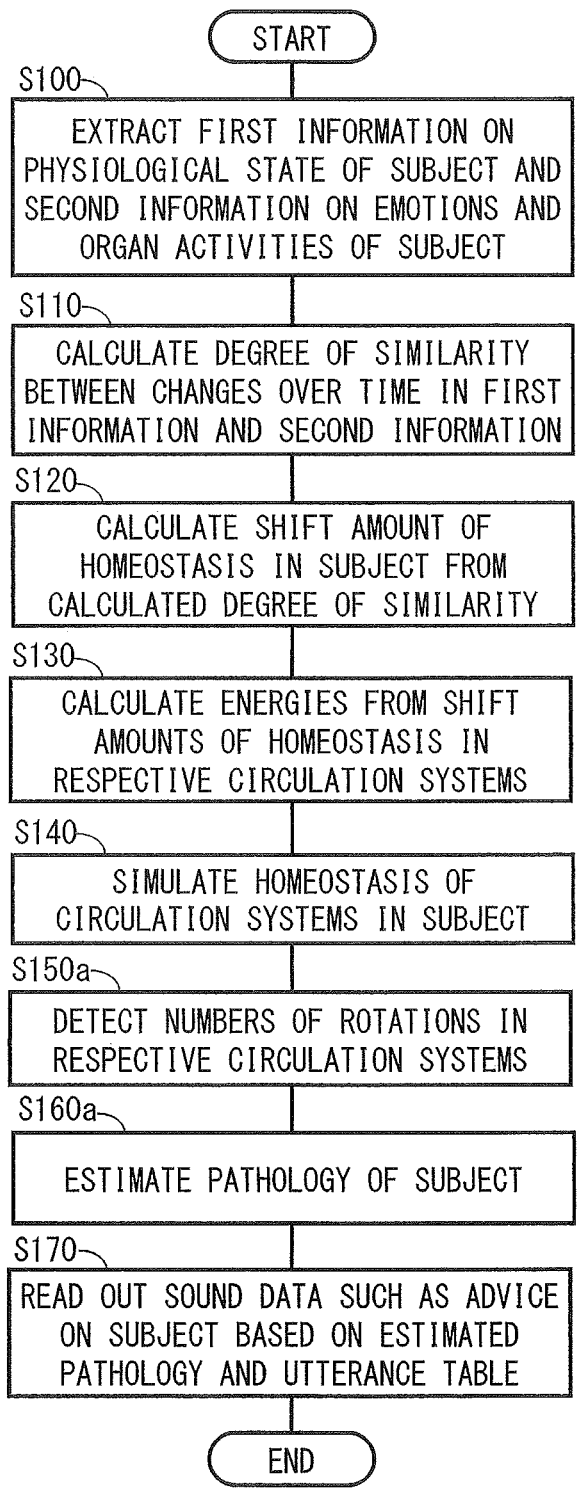
FIG. 32 is a diagram illustrating an example of an estimation process which is performed by the estimation device illustrated in FIG. 30.

FIG. 32 illustrates an example of an estimation process performed by the estimation device 100c illustrated in FIG. 30. Meanwhile, among processes of steps illustrated in FIG. 30, the same step number will be attached to steps indicating processes that are the same as or similar to those of the steps illustrated in FIG. 29, and a detailed description thereof will be omitted. Step S100 to step S140, step S150a, step S160a, and step S170 are realized by a CPU, mounted on the estimation device 100c, executing an estimation program. That is, FIG. 32 illustrates an estimation program and an estimation method according to another embodiment. In this case, the extraction unit 10a, the calculation unit 20a, the estimation unit 30c, and the examination unit 40a illustrated in FIG. 30 are realized by executing an estimation program. Meanwhile, processes illustrated in FIG. 32 may be realized by hardware mounted on the estimation device 100c. In this case, the extraction unit 10a, the calculation unit 20a, the estimation unit 30c, and the examination unit 40a illustrated in FIG. 30 are realized by circuits disposed within the estimation device 100c.

The estimation device 100c performs processes of step S100 to step S140, step S150a, and step S160a illustrated in FIG. 32 and then performs a process of step S170.

In step S170, the estimation unit 30c reads out sound data such as an advice on a subject PA based on the pathology estimated in step S160a and the utterance table 80, as described in FIG. 31. The estimation unit 30c outputs the read-out sound data to the output device 2a.

In addition, the estimation process performed by the estimation device 100c is terminated. The output device 2a displays a shift amount of homeostasis together with a result of the estimated pathology. In addition, the output device 2a outputs sound data received from the estimation device 100c from a speaker to thereby perform the utterance of an advice or the like according to a pathology estimated with respect to a subject PA. Meanwhile, the output device 2a may represent the magnitude of a shift amount of homeostasis, that is, the degree of a symptom of the estimated pathology or a degree indicating the health of the subject PA by a color or a facial expression of a person, an animal, or the like of an animation, and may display the magnitude on a display. In addition, the output device 2a may display a person, an animal, or the like of an animation on the display, and may output received sound data as if the displayed person or animal is uttering.

Meanwhile, a flow illustrated in FIG. 32 may be repeatedly performed whenever an instruction is given from a doctor or a subject PA, or may be performed at a predetermined frequency.

As described above, in the embodiment illustrated in FIGS. 30 to 32, a shift amount of homeostasis in a subject PA is calculated using first information indicating a physiological state of the subject PA and second information indicating an emotion and organ activity of the subject PA. Thereby, the estimation device 100c can easily estimate the pathology of the subject PA without having expert knowledge on medicine with reference to an index such as a shift amount of the homeostasis. In addition, the estimation device 100c performs simulation of homeostasis of the subject PA using a shift amount of homeostasis in each circulation system Ka as an input energy. The estimation device 100c compares the frequency of appearance of the number of rotations in each circulation system Ka which indicates a change in the homeostasis detected from the performed simulation with the frequency of appearance of the number of rotations in each circulation system Ka which is indicated when a subject PA is healthy. In addition, the estimation device 100c can estimate the pathology of the subject PA with a higher level of accuracy than in the related art, using a comparison result and the pathology table 70.

In addition, the estimation device 100c may perform the utterance of an advice or the like and then may measure the physiology of a subject PA again and estimate the state of the subject PA. In addition, the estimation device 100c may evaluate an effect of the utterance of an advice or the like based on an estimation result, and may perform correction or the like of contents of the advice or the like which are stored in a storage region of utterance in the utterance table 80 based on the evaluation. Thereby, the estimation device 100c can perform finer treatment on the subject PA than in the related art.

Meanwhile, a description has been given of a case where the estimation device 100 (100a, 100b, 100c) is applied to psychological counseling such as psychoanalysis, behavior prediction, or behavior analysis and an interview or prescription in psychiatric care or general medical care, but the invention is not limited thereto. For example, the estimation device 100 may be applied to a robot, artificial intelligence, a vehicle, a call center, entertainment, the Internet, a portable terminal device application or service of a smart phone, a tablet type terminal, or the like, and a retrieval system. In addition, the estimation device 100 may be applied to a diagnostic device, an automatic inquiry device, a disaster triage, and the like. In addition, the estimation device 100 may be applied to a financial credit management system, behavior prediction, a company, a school, a government agency, a police, the military, information analysis in information collection activity or the like, psychological analysis leading to false discovery, and organization group management. In addition, the estimation device 100 may be applied to a system for managing the health of the mind and behavior prediction of a member of an organization, a researcher, an employee, a manager, or the like, a system for controlling environment such as a house, an office, an airplane, or a spacecraft, or means for knowing the state of the mind or behavior prediction of a family member or a friend. In addition, the estimation device 100 may be applied to music, movie distribution, general information retrieval, information analysis management, information processing, or customer sensibility preference market analysis, a system that manages these through a network or on a stand-alone basis, and the like. The many features and advantages of the embodiments are apparent from the detailed specification and, thus, it is intended by the appended claims to cover ad such features and advantages of the embodiments that fall within the true spirit and scope thereof. Further, since numerous modifications and Changes will readily occur to those skilled in the art, it is not desired to limit the inventive embodiments to exact construction and operation illustrated and described, and accordingly ad suitable modifications and equivalents may be resorted to, fading within the scope thereof.

The invention claimed is:

1. An estimation device comprising:
an extraction unit extracting first information on a physiological state of a subject and second information on at least one of an emotion and organ activity of the subject from information on a physiology of the subject;
a first calculation unit calculating, for each of a plurality of emotions set in advance, a mutual correlation coefficient indicating a degree of similarity between changes over time of the extracted first information and the second information;
a second calculation unit calculating, for each of the plurality of emotions, a shift amount from a predetermined state in which a homeostasis in the subject is maintained based on the mutual correlation coefficient calculated for each of the plurality of emotions;
an examination unit calculating energy acting on the emotion and the organ activity of the subject using an energy function having the shift amount calculated for each of the plurality of emotions as its variable, and obtaining the changes over time in the homeostasis in the subject by using the calculated energy and a calculation model indicating a living body of the subject; and
an estimation unit estimating a pathology of the subject by obtaining a difference between the changes over time in the homeostasis of the subject obtained by the examination unit and changes over time in the homeostasis when the subject is healthy, and according to the obtained difference, wherein
the plurality of emotions are anger, pleasure and sorrow, and
the energy function is $E(K1)=\text{sqrt}(\alpha \times \alpha + \beta \times \beta + \gamma \times \gamma)$, where $\alpha$ is the shift amount calculated for anger, $\beta$ is the shift amount calculated for pleasure and $\gamma$ is the shift amount calculated for sorrow.

2. The estimation device according to claim 1, further comprising
an input unit receiving a sound signal from the subject as the information indicating the physiology of the subject.

3. The estimation device according to claim 2, further comprising
a storage unit storing sound data of an advice on the subject for each pathology, wherein
the estimation unit selects sound data of the advice on the subject based on the pathology of the subject being estimated and outputs the sound data being selected to an external output device.

4. The estimation device according to claim 1, further comprising
an input unit receiving the organ activity of the subject as the information on a physiology of the subject.

5. The estimation device according to claim 4, further comprising
a storage unit storing sound data of an advice on the subject for each pathology, wherein
the estimation unit selects sound data of the advice on the subject based on the pathology of the subject being estimated and outputs the sound data being selected to an external output device.

6. The estimation device according to claim 1, further comprising
a storage unit storing sound data of an advice on the subject for each pathology, wherein
the estimation unit selects sound data of the advice on the subject based on the pathology of the subject being estimated and outputs the sound data being selected to an external output device.

7. A non-transitory storage medium storing a program causing a computer to execute:
extracting first information on a physiological state of a subject and second information on at least one of an emotion and organ activity of the subject from information on a physiology of the subject;
calculating, for each of a plurality of emotions set in advance, a mutual correlation coefficient indicating a degree of similarity between changes over time of the extracted first information and the second information;
calculating, for each of the plurality of emotions, a shift amount from a predetermined state in which a homeostasis in the subject is maintained based on the mutual correlation coefficient calculated for each of the plurality of emotions;
calculating energy acting on the emotion and the organ activity of the subject using an energy function having the shift amount calculated for each of the plurality of emotions as its variable;
obtaining the changes over time in the homeostasis in the subject by using the calculated energy and a calculation model indicating a living body of the subject; and
estimating a pathology of the subject by obtaining a difference between the obtained changes over time in the homeostasis of the subject and changes over time in the homeostasis when the subject is healthy, and according to the obtained difference, wherein
the plurality of emotions are anger, pleasure and sorrow, and
the energy function is $E(K1)=\text{sqrt}(\alpha \times \alpha + \beta \times \beta + \gamma \times \gamma)$, where $\alpha$ is the shift amount calculated for anger, $\beta$ is the shift amount calculated for pleasure and $\gamma$ is the shift amount calculated for sorrow.

8. An estimation method comprising:
extracting first information on a physiological state of a subject and second information on at least one of an emotion and organ activity of the subject from information on a physiology of the subject;
calculating, for each of a plurality of emotions set in advance, a mutual correlation coefficient indicating a degree of similarity between changes over time of the extracted first information and the second information;
calculating, for each of the plurality of emotions, a shift amount from a predetermined state in which a homeostasis in the subject is maintained based on the mutual correlation coefficient calculated for each of the plurality of emotions;
calculating energy acting on the emotion and the organ activity of the subject using an energy function having the shift amount calculated for each of the plurality of emotions as its variable;
obtaining the changes over time in the homeostasis in the subject by using the calculated energy and a calculation model indicating a living body of the subject; and
estimating a pathology of the subject by obtaining a difference between the obtained changes over time in the homeostasis of the subject and changes over time in the homeostasis when the subject is healthy, and according to the obtained difference, wherein the plurality of emotions are anger, pleasure and sorrow, and
the energy function is $E(K1)=\text{sqrt}(\alpha \times \alpha + \beta \times \beta + \gamma \times \gamma)$, where $\alpha$ is the shift amount calculated for anger, $\beta$ is the shift amount calculated for pleasure and $\gamma$ is the shift amount calculated for sorrow.

9. An estimation system comprising:
a measurement device measuring a physiology of a subject;
an estimation device estimating a pathology of the subject using information on the physiology of the subject which is measured by the measurement device; and
an output device outputting a result of the pathology estimated by the estimation device, wherein
the estimation device includes:
an extraction unit extracting first information on a physiological state of a subject and second information on at least one of an emotion and organ activity of the subject from information on a physiology of the subject;
a first calculation unit calculating, for each of a plurality of emotions set in advance, a mutual correlation coefficient indicating a degree of similarity between changes over time of the extracted first information and the second information;
a second calculation unit calculating, for each of the plurality of emotions, a shift amount from a predetermined state in which a homeostasis in the subject is maintained based on the mutual correlation coefficient calculated for each of the plurality of emotions;
an examination unit calculating energy acting on the emotion and the organ activity of the subject using an energy function having the shift amount calculated for each of the plurality of emotions as its variable, and obtaining the changes over time in the homeostasis in the subject by using the calculated energy and a calculation model indicating a living body of the subject; and
an estimation unit estimating a pathology of the subject by obtaining a difference between the changes over time in the homeostasis of the subject obtained by the examination unit and changes over time in the homeostasis when the subject is healthy, and according to the obtained difference, wherein
the plurality of emotions are anger, pleasure and sorrow, and
the energy function is $E(K1)=\text{sqrt}(\alpha \times \alpha + \beta \times \beta + \gamma \times \gamma)$, where $\alpha$ is the shift amount calculated for anger, $\beta$ is the shift amount calculated for pleasure and $\gamma$ is the shift amount calculated for sorrow.

10. An estimation device comprising:
an extraction unit extracting first information on a physiological state of a subject and second information on at least one of an emotion and organ activity of the subject from information on a physiology of the subject;
a first calculation unit calculating, for each of a plurality of emotions set in advance, a mutual correlation coefficient indicating a degree of similarity between changes over time of the extracted first information and the second information;
a second calculation unit calculating, for each of the plurality of emotions, a shift amount from a predetermined state in which a homeostasis in the subject is maintained based on the mutual correlation coefficient calculated for each of the plurality of emotions;
a third calculation unit calculating a balanced position at which each of the plurality of emotions is balanced in a predetermined coordinate system having each of the plurality of emotions as its axes, by using the mutual correlation coefficient of the each of the plurality of emotions, and then calculating a distance between a center of the predetermined coordinate system and the balanced position; and an estimation unit estimating a pathology of the subject by using the shift amount calculated for each of the emotions and the distance, wherein the plurality of emotions are anger, pleasure and sorrow.

11. The estimation device according to claim 10, further comprising an input unit receiving a sound signal from the subject as the information indicating the physiology of the subject.

12. The estimation device according to claim 10, further comprising an input unit receiving the organ activity of the subject as the information on a physiology of the subject.

13. The estimation device according to claim 10, further comprising a storage unit storing sound data of an advice on the subject for each pathology, wherein the estimation unit selects sound data of the advice on the subject based on the pathology of the subject being estimated and outputs the sound data being selected to an external output device.

14. A non-transitory storage medium storing a program causing a computer to execute:

extracting first information on a physiological state of a subject and second information on at least one of an emotion and organ activity of the subject from information on a physiology of the subject;

calculating, for each of a plurality of emotions set in advance, a mutual correlation coefficient indicating a degree of similarity between changes over time of the extracted first information and the second information;

calculating, for each of the plurality of emotions, a shift amount from a predetermined state in which a homeostasis in the subject is maintained based on the mutual correlation coefficient calculated for each of the plurality of emotions;

calculating a balanced position at which each of the plurality of emotions is balanced in a predetermined coordinate system having each of the plurality of emotions as its axes, by using the mutual correlation coefficient of the each of the plurality of emotions, and then calculating a distance between a center of the predetermined coordinate system and the balanced position; and estimating a pathology of the subject by using the shift amount calculated for each of the emotions and the distance, wherein the plurality of emotions are anger, pleasure and sorrow.

15. An estimation method comprising:

extracting first information on a physiological state of a subject and second information on at least one of an emotion and organ activity of the subject from information on a physiology of the subject;

calculating, for each of a plurality of emotions set in advance, a mutual correlation coefficient indicating a degree of similarity between changes over time of the extracted first information and the second information;

calculating, for each of the plurality of emotions, a shift amount from a predetermined state in which a homeostasis in the subject is maintained based on the mutual correlation coefficient calculated for each of the plurality of emotions;

calculating a balanced position at which each of the plurality of emotions is balanced in a predetermined coordinate system having each of the plurality of emotions as its axes, by using the mutual correlation coefficient of the each of the plurality of emotions, and then calculating a distance between a center of the predetermined coordinate system and the balanced position; and estimating a pathology of the subject by using the shift amount calculated for each of the emotions and the distance, wherein the plurality of emotions are anger, pleasure and sorrow.

16. An estimation system comprising:

a measurement device measuring a physiology of a subject;

an estimation device estimating a pathology of the subject using information on the physiology of the subject which is measured by the measurement device; and an output device outputting a result of the pathology estimated by the estimation device, wherein the estimation device includes:

an extraction unit extracting first information on a physiological state of a subject and second information on at least one of an emotion and organ activity of the subject from information on a physiology of the subject;

a first calculation unit calculating, for each of a plurality of emotions set in advance, a mutual correlation coefficient indicating a degree of similarity between changes over time of the extracted first information and the second information;

a second calculation unit calculating, for each of the plurality of emotions, a shift amount from a predetermined state in which a homeostasis in the subject is maintained based on the mutual correlation coefficient calculated for each of the plurality of emotions;

a third calculation unit calculating a balanced position at which each of the plurality of emotions is balanced in a predetermined coordinate system having each of the plurality of emotions as its axes, by using the mutual correlation coefficient of the each of the plurality of emotions, and then calculating a distance between a center of the predetermined coordinate system and the balanced position; and an estimation unit estimating a pathology of the subject by using the shift amount calculated for each of the emotions and the distance, wherein the plurality of emotions are anger, pleasure and sorrow.

* * * * *